United States Patent
Oida et al.

(10) Patent No.: US 11,874,348 B2
(45) Date of Patent: Jan. 16, 2024

(54) BRAIN MEASUREMENT SYSTEM

(71) Applicants: HAMAMATSU PHOTONICS K.K., Hamamatsu (JP); Kyoto University, Kyoto (JP)

(72) Inventors: Takenori Oida, Hamamatsu (JP); Takahiro Moriya, Hamamatsu (JP); Akinori Saito, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 0 days.

(21) Appl. No.: 17/891,467

(22) Filed: Aug. 19, 2022

(65) Prior Publication Data

US 2023/0061021 A1 Mar. 2, 2023

(30) Foreign Application Priority Data

Aug. 30, 2021 (JP) .................. 2021-140108

(51) Int. Cl.
*G01R 33/3415* (2006.01)
*A61B 5/055* (2006.01)
*G01R 33/385* (2006.01)

(52) U.S. Cl.
CPC .......... *G01R 33/3415* (2013.01); *A61B 5/055* (2013.01); *G01R 33/385* (2013.01)

(58) Field of Classification Search
CPC .. G01R 33/3415; G01R 33/385; G01R 33/26; G01R 33/3628; G01R 33/4808; G01R 33/4835; A61B 5/055
See application file for complete search history.

(56) References Cited

U.S. PATENT DOCUMENTS 8,305,078 B2 11/2012 Savukov et al.
8,519,705 B2 8/2013 Savukov et al.
(Continued)

FOREIGN PATENT DOCUMENTS

JP 5823195 B2 11/2015

OTHER PUBLICATIONS

Boto, Elena et al., "Moving magnetoencephalography towards real-world applications with a wearable system," Nature, vol. 555, Mar. 29, 2018, pp. 657-661.
(Continued)

*Primary Examiner* — G. M. A Hyder
(74) *Attorney, Agent, or Firm* — Faegre Drinker Biddle & Reath LLP

(57) ABSTRACT

Provided is a brain measurement system including: a geomagnetic correction coil; a geomagnetic gradient correction coil; a transmission coil; a receiving coil; a plurality of resonance adjustment circuits; a plurality of OPM modules provided corresponding to each of the plurality of resonance adjustment circuits for detecting a signal having a resonance frequency output from the resonance adjustment circuit; and a control device for generating an MR image based on the signal detected by the OPM module, wherein, when a direction parallel to a central axis of a head portion of a subject is defined as a Z-axis direction, the resonance frequency related to each of the plurality of resonance adjustment circuits is set according to a magnetic field gradient in the Z-axis direction generated by control of a position of the corresponding receiving coil in the Z-axis direction and a tilted magnetic field.

5 Claims, 13 Drawing Sheets

(56) References Cited

U.S. PATENT DOCUMENTS

2021/0386347 A1* 12/2021 Moriya ................ G01R 33/26
2021/0389400 A1* 12/2021 Oida ................ G01R 33/4215

OTHER PUBLICATIONS

Iivanainen, Joonas et al., "On-scalp MEG system utilizing an actively shielded array of optically-pumped magnetometers," NeuroImage 194, 2019, pp. 244-258.

Körber, Rainer et al., "SQUIDs in biomagnetism: a roadmap towards improved healthcare," Superconductor Science and Technology, 29, 2016, pp. 1-30.

Sarracanie, Mathieu et al., "Low-Cost High-Performance MRI," Scientific Reports, 5:15177, 2015, pp. 1-9.

Tsai, L. L. et al., "An Open-Access, Very-Low-Field MRI System for Posture-Dependent $^3$He Human Lung Imaging," J Magn Reson. 193(2), Aug. 2008, pp. 274-285.

\* cited by examiner

NOISE LEVEL 23 fT/Hz$^{1/2}$@300kHz

NOISE LEVEL 2.1 fT/Hz$^{1/2}$@300kHz

BRAIN MEASUREMENT SYSTEM

TECHNICAL FIELD

The present disclosure relates to a brain measurement system.

BACKGROUND

In the related art, as a magnetoencephalographic system, a superconducting quantum interference device (SQUID) has been used to measure a minute brain magnetic field. In recent years, a magnetoencephalographic system using an optically pumped magnetometer instead of the SQUID has been studied. The optically pumped magnetometer measures a minute magnetic field by detection using spin polarization of alkali metal atoms excited by optical pumping. For example, Patent Document 1 (Japanese Patent No. 5823195) discloses a magnetoencephalographic system using an optical pumping magnetometer. Recently, research has also been performed to integrate a magnetoencephalographic system and a magnetic resonance imaging (MRI) device using a SQUID ("Squids in biomagnetism: a roadmap towards improved healthcare", Supercond. Sci. Technol. 29 (2016) 113001 (30 pp)).

Herein, in a brain measurement system such as an MRI, it is important to improve a detection sensitivity. However, generally, when the detection sensitivity is improved, a frequency band (that is, a field of view (FOV)) that can be detected is usually narrowed. As described above, in the related art, it has been difficult for the brain measurement system to achieve both the detection sensitivity and the sufficient FOV.

The disclosure has been made in view of the above circumstances, and an object thereof is to provide a brain measurement system capable of improving a detection sensitivity and ensuring a sufficient FOV.

SUMMARY

A brain measurement system according to one aspect of the disclosure includes: a static magnetic field coil for applying a static magnetic field; a gradient magnetic field coil for applying a gradient magnetic field; a transmission coil for transmitting a transmission pulse having a predetermined frequency; a plurality of receiving coils for detecting a nuclear magnetic resonance signal generated by transmission of the transmission pulse and converting the nuclear magnetic resonance signal into a current; a plurality of resonance adjustment circuits provided corresponding to each of the plurality of receiving coils for outputting a signal having a predetermined resonance frequency of a current output from the receiving coil; a plurality of detection units provided corresponding to each of the plurality of resonance adjustment circuits for detecting the signal having the resonance frequency output from the resonance adjustment circuit; and a control device that controls currents to be supplied to the static magnetic field coil and the gradient magnetic field coil to control the static magnetic field and the tilted magnetic field and controls a current to be supplied to the transmission coil so that the transmission pulse is transmitted to a head portion of a subject to generate an MR image based on the signal detected by the detection unit, wherein, when a direction parallel to a central axis of the head portion of the subject is defined as a Z-axis direction, the resonance frequency related to each of the plurality of resonance adjustment circuits is set according to the magnetic field gradient in the Z-axis direction generated by control of a position of the corresponding receiving coil in the Z-axis direction and the tilted magnetic field.

The brain measurement system according to one aspect of the disclosure is provided with a resonance adjustment circuit that extracts a signal having a predetermined resonance frequency of the current output from the receiving coil. The resonance frequency of each of the plurality of resonance adjustment circuits is set according to the position of the corresponding receiving coil in the Z-axis direction and the magnetic field gradient in the Z-axis direction. In this manner, by setting the resonance frequency of the resonance adjustment circuit in consideration of the position of the corresponding receiving coil and the generated magnetic field gradient, the sensitivity of the signal detected in the detection unit provided corresponding to the resonance adjustment circuit can be improved. Herein, when the sensitivity is improved by the resonance adjustment circuit, the frequency band is limited to about several kHz. In this respect, in the brain measurement system according to one aspect of the disclosure, since the plurality of receiving coils having different resonance frequencies are arranged according to the magnetic field gradient, it is possible to ensure a sufficient frequency band, that is, a field of view (FOV) as a whole while improving the sensitivity. As described above, according to the brain measurement system related to one aspect of the disclosure, it is possible to improve a detection sensitivity and ensure a sufficient FOV.

The plurality of detection units may include one detection unit that detects all the signals related to the two or more receiving coils having the same resonance frequency related to the resonance adjustment circuit by adjusting the phases. In this manner, the signals related to the receiving coils having the same resonance frequency are detected by the same detection unit while adjusting the phase, so that the brain measurement can be performed with a simple configuration by reducing the number of detection units.

The frequency band in which the detection sensitivity of the detection unit is maximized may include the resonance frequency related to the corresponding resonance adjustment circuit. Accordingly, it is possible to further improve the detection sensitivity in the detection unit.

The receiving coil may be formed so that the maximum area and the number of turns on a plane perpendicular to the direction in which the static magnetic field is to be generated are constant. With such a configuration, the sensitivity of the receiving coil becomes uniform, and brain measurement can be more appropriately performed.

The receiving coil may be a phased array coil. With such a configuration, the induced electromotive forces from the adjacent coils can be cancelled to minimize the electrical interference, so that the brain measurement can be performed.

According to the disclosure, it is possible to provide the brain measurement system capable of improving the detection sensitivity and ensuring sufficient FOV.

DETAILED DESCRIPTION

Figure 1:
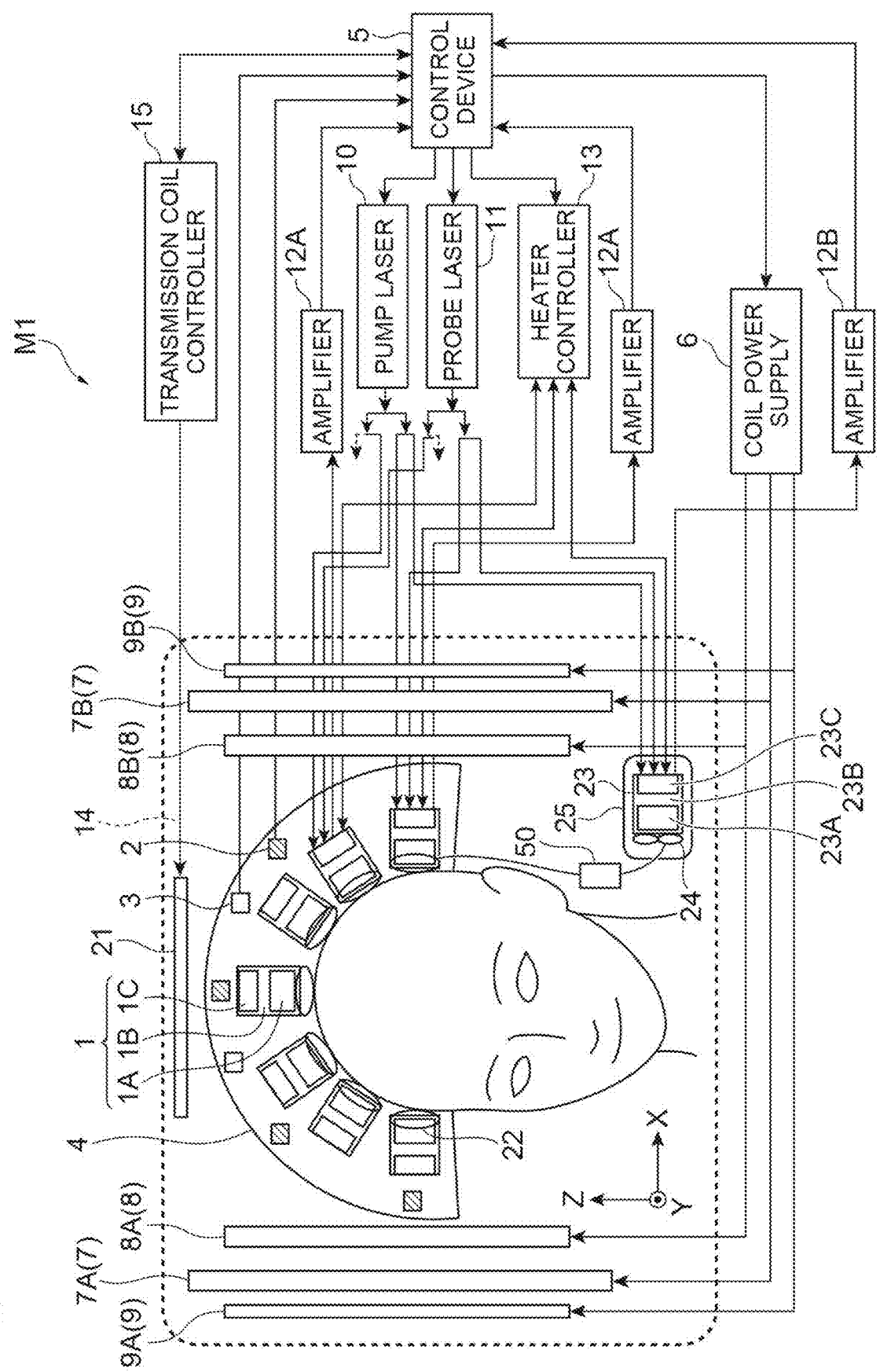
FIG. 1 is a schematic diagram illustrating a configuration of a brain measurement system according to an embodiment.

Hereinafter, embodiments for performing the disclosure will be described in detail with reference to accompanying drawings. In the description of the drawings, the same elements are denoted by the same reference numerals, and duplicate description is omitted.

[Basic Configuration of Brain Measurement System]

FIG. 1 is a schematic diagram illustrating a configuration of a brain measurement system M1 according to an embodiment. The brain measurement system M1 is an example of an AC magnetic field measurement device and is a device measuring a brain magnetic field and measuring a magnetic resonance (MR) image for a subject. The brain measurement system M1 includes a magnetoencephalographic system module having a plurality of optically pumped magnetometer (OPM) modules 1, a plurality of geomagnetic-correction magnetic sensors 2, a plurality of active shield magnetic sensors 3, a non-magnetic frame 4, a pair of geomagnetic correction coils 7, a pair of geomagnetic gradient correction coils 8, and a pair of fluctuating magnetic field correction coils 9 and an MRI module having a transmission coil 21, a plurality of receiving coils 22, a plurality of OPM modules 23 (detection units), a plurality of output coils 24, and a plurality of resonance adjustment circuits 50. It is noted that the OPM module 23 as a detection unit may be replaced by an amplifier (not illustrated). Furthermore, the brain measurement system M1 includes a control device 5, a coil power supply 6, a pump laser 10, a probe laser 11, amplifiers 12A and 12B, a heater controller 13, an electromagnetic shield 14, a transmission coil controller 15, and the like. It is noted that in the description with reference to FIG. 1, the description of the resonance adjustment circuit 50 will be omitted (the resonance adjustment circuit 50 will be described later).

In the following description, the direction substantially parallel to the central axis of the head portion of the subject is defined as a Z-axis direction, and the directions perpendicular to the Z-axis and perpendicular to each other are defined as an X-axis direction and a Y-axis direction.

The OPM module 1 includes an optically pumped magnetometer 1A, a heat insulating material 1B, and a readout circuit 1C. The plurality of OPM modules 1 are arranged at predetermined intervals along, for example, the scalp.

The optically pumped magnetometer 1A is a sensor that measures a brain magnetic field by using optical pumping and has a sensitivity of, for example, about 10 fT to 10 pT. The heat insulating material 1B prevents heat transfer and heat transmission of the optically pumped magnetometer 1A. The readout circuit 1C is a circuit for acquiring a detection result of the optically pumped magnetometer 1A. The optically pumped magnetometer 1A brings the alkali metal into the excited state by irradiating a cell enclosing an alkali metal vapor with pump light. The excited alkali metal is in the spin-polarization state, and when the excited alkali metal receives magnetism, the inclination of the spin-polarization axis of the alkali metal atom changes according to the magnetism. The inclination of the spin-polarization axis is detected by probe light irradiated separately from the pump light. It is noted that the optically pumped magnetometer 1A is configured so that the predetermined bias magnetic field is applied in the irradiation direction of the pump light so as to be sensitive to the magnetic field having a frequency included in a range of 0 to 200 Hz. The readout circuit 1C receives the probe light passing through the alkali metal vapor by the photodiode and acquires the detection result. The readout circuit 1C outputs the detection result to the amplifier 12A.

The optically pumped magnetometer 1A may be, for example, an axial gradiometer. The axial gradiometer has a measurement area and a reference area in the direction perpendicular to the scalp (measurement point) of the subject and coaxially. The measurement area is, for example, a site closest to the scalp of the subject among the sites where the axial gradiometer measures the brain magnetic field. The reference area is, for example, a site which is in a predetermined distance (for example, 3 cm) from the measurement area with respect to the direction away from the scalp of the subject among the sites where the axial gradiometer measures the brain magnetic field. The axial gradiometer outputs respective measurement results in the measurement area and the reference area to the amplifier 12A. Herein, when common mode noise is included, the influence is exhibited in each of an output result in the measurement area and an output result in the reference area. The common mode noise is removed by acquiring the difference between the output result in the measurement area and the output result in the reference area. For example, during the measurement under the magnetic noise environment of 1 pT, the optically pumped magnetometer 1A can obtain a sensitivity of about 10 fT/Hz by removing the common mode noise.

The geomagnetic-correction magnetic sensor 2 is a sensor that measures a magnetic field related to a geomagnetism at the position corresponding to the optically pumped magnetometer 1A and is configured with, for example, a fluxgate sensor having a sensitivity of about 1 nT to 100 pT. The position corresponding to the optically pumped magnetometer 1A is a position around (near) the area where the optically pumped magnetometer 1A is arranged. The geomagnetic-correction magnetic sensor 2 may be provided in a one-to-one correspondence with the optically pumped magnetometer 1A or may be provided in a one-to-many correspondence (one geomagnetic-correction magnetic sensor 2 to the plurality of optically pumped magnetometers 1A). The geomagnetic-correction magnetic sensor 2 measures, for example, a geomagnetism and a gradient magnetic field of the geomagnetism (hereinafter, simply referred to as a "gradient magnetic field") as a magnetic field related to the geomagnetism and outputs a measured value to the control device 5. The measured value of the geomagnetic-correction magnetic sensor 2 can be represented by a vector having a direction and a magnitude. The geomagnetic-correction magnetic sensor 2 may continuously perform measurement and output at predetermined time intervals.

The active shield magnetic sensor 3 is a sensor that measures a fluctuating magnetic field at a position corresponding to the optically pumped magnetometer 1A, has a sensitivity of, for example, 100 fT to 10 nT, and is configured with an optically pumped magnetometer different from the optically pumped magnetometer 1A. The position corresponding to the optically pumped magnetometer 1A is a position around (near) the area where the optically pumped magnetometer 1A is arranged. The active shield magnetic sensor 3 may be provided in a one-to-one correspondence with the optically pumped magnetometer 1A or may be provided in a one-to-many correspondence (one active shield magnetic sensor 3 to the plurality of optically pumped magnetometers 1A). The active shield magnetic sensor 3 measures the magnetic field of the noise (alternating current) component of, for example, 200 Hz or less as a fluctuating magnetic field and outputs the measured value to the control device 5. The measured value of the active shield magnetic sensor 3 can be represented by a vector having a direction and a magnitude. The active shield magnetic sensor 3 may continuously perform measurement and output at predetermined time intervals.

The non-magnetic frame 4 is a frame that covers the entire area of the scalp of the subject of which brain magnetic field is to be measured and is made of a non-magnetic material such as graphite of which relative permeability is close to 1 and does not disturb a magnetic field distribution. The non-magnetic frame 4 can be, for example, a helmet-type frame that surrounds the entire area of the scalp of the subject and is attached to the head portion of the subject. The plurality of optically pumped magnetometers 1A are fixed to the non-magnetic frame 4 so as to be close to the scalp of the subject. Furthermore, the geomagnetic-correction magnetic sensor 2 is fixed to the non-magnetic frame 4 so that the magnetic field related to the geomagnetism at each position of the plurality of optically pumped magnetometers 1A can be measured, and the active shield magnetic sensor 3 is fixed to the non-magnetic frame 4 so that the fluctuating magnetic field at each position of the plurality of optically pumped magnetometers 1A can be measured. Since a variation of the magnetic field strength depending on the position of the fluctuating magnetic field is smaller than that of the static magnetic field, the geomagnetic-correction magnetic sensors 2 and the active shield magnetic sensors 3 may be fixed to the non-magnetic frame 4 so that the number of active shield magnetic sensors 3 is smaller than the number of geomagnetic-correction magnetic sensors 2. In addition, the receiving coil 22 for detecting a nuclear magnetic resonance signal to measure an MR image is fixed to the scalp side of the subject of the plurality of optically pumped magnetometers 1A in the non-magnetic frame 4. The receiving coil 22 detects the nuclear magnetic resonance signal of the proton to be described later and converts the nuclear magnetic resonance signal into the current. In order to improve a detection sensitivity of the nuclear magnetic resonance signal, it is desirable that the receiving coil 22 is provided on the side of the optically pumped magnetometer 1A near the scalp of the head portion of the subject.

The receiving coil 22 is formed so that the maximum area and the number of turns on a plane perpendicular to the X-axis direction (details will be described later) which is the direction in which the static magnetic field is to be generated are constant. The maximum area is determined, for example, by the size, shape (ellipse), position, axis direction, and the like of the receiving coil 22. With such a configuration, the sensitivity of the receiving coil 22 becomes uniform.

The transmission coil 21 is a coil that irradiates the head portion of the subject with an RF pulse (transmission pulse) having a predetermined frequency (for example, about 300 kHz) during the measurement of the MR image. The transmission coil 21 is arranged, for example, above the head portion of the subject outside the non-magnetic frame 4.

The output coil 24 is electrically connected to both ends of the receiving coil 22 via a cable to receive the current flowing through both ends of the receiving coil 22, convert the current into the magnetic signal again, and outputs the magnetic signal. In addition, although the output coil 24 and the receiving coil 22 are connected in detail via the resonance adjustment circuit 50, herein, the description of the resonance adjustment circuit 50 will be omitted (the resonance adjustment circuit 50 will be described later).

Similarly to the OPM module 1, the OPM module 23 includes an optically pumped magnetometer 23A, a heat insulating material 23B, and a readout circuit 23C. Together with the output coil 24, the OPM module 23 is housed and arranged, for example, outside the non-magnetic frame 4 in the magnetic shield 25 that shields the static magnetic field to be described later. The magnetic shield 25 is made of, for example, a mu-metal having a relative permeability of more than 1.

The optically pumped magnetometer 23A is a sensor that measures a magnetic signal by using optical pumping. It is noted that the optically pumped magnetometer 23A is configured so that the predetermined bias magnetic field is applied in the irradiation direction of the pump light so as to be sensitive to the magnetic field having a frequency included in a range of 20 kHz to 500 kHz. For example, the bias magnetic field of about 40 pT is applied so as to be sensitive to the frequency of 300 kHz of the electromagnetic wave emitted by the proton. The readout circuit 23C outputs the detection result by the optically pumped magnetometer 23A to the amplifier 12B.

Figure 2:
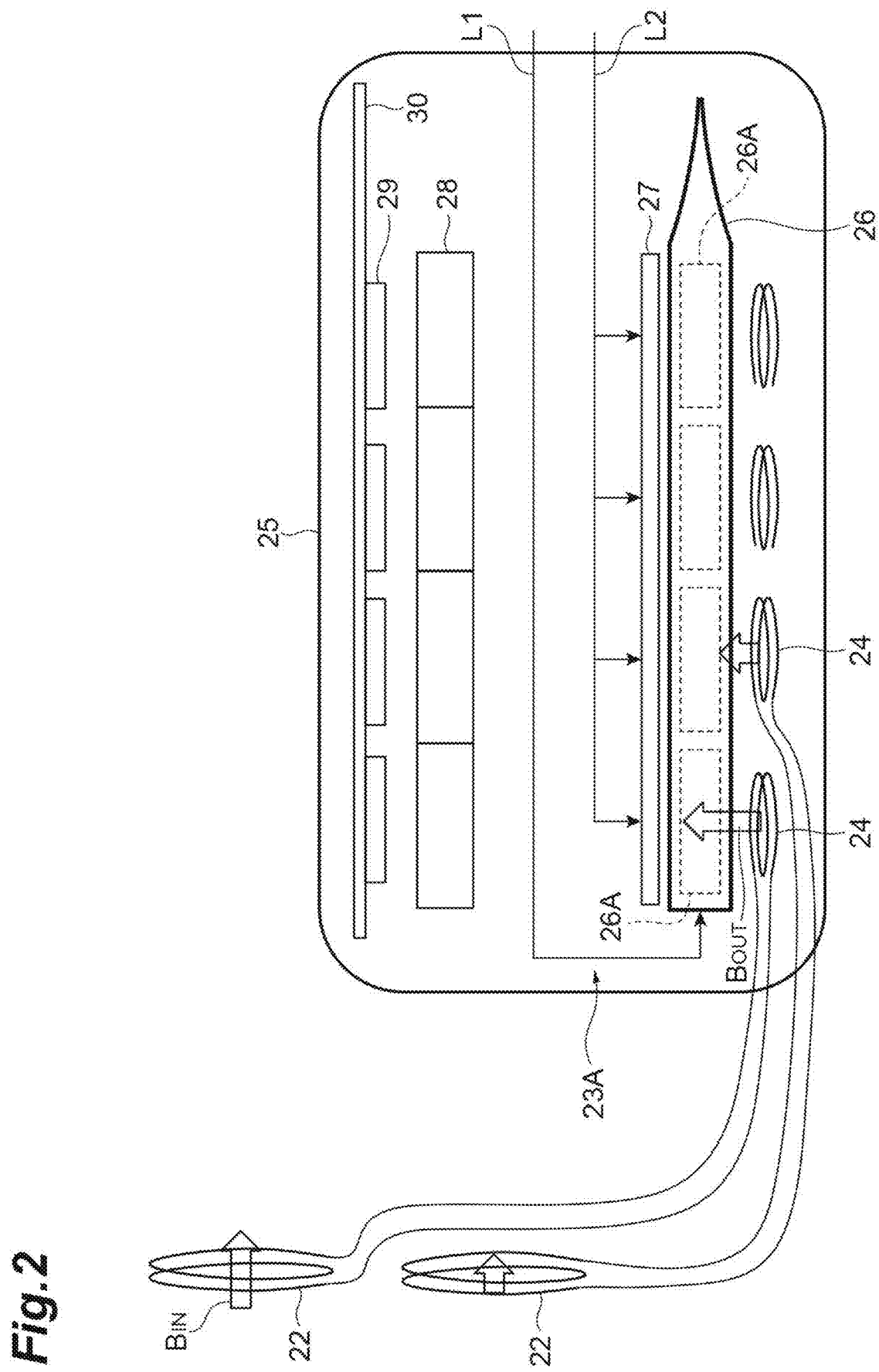
FIG. 2 is a schematic diagram illustrating a configuration of an OPM module 23 according to the embodiment.

FIG. 2 illustrates a specific example of the configuration of the OPM module 23. The optically pumped magnetometer 23A includes a longitudinal-shape cell 26 enclosing a gas containing an alkali metal of which direction of polarization changes depending on a magnetic field to be measured, a heater 27 that heats the entire cell 26 to a predetermined temperature (for example, 180 degrees), a polarization beam splitter 28, and a photodetector 29. Pump light L1 from the outside is introduced into the cell 26 along the longitudinal direction inside the cell 26, and each of crossing areas 26A in which the cell is divided into the plurality of cells (for example, quadrant) in the longitudinal direction along the direction perpendicular to the longitudinal direction is irradiated with branched probe light L2 from the outside. A magnetic rotation angle of the probe light L2 transmitting through these crossing areas 26A is detected by the polarization beam splitter 28 and the photodetector 29 provided corresponding to each of the crossing areas 26A. That is, the polarization beam splitter 28 separates the probe light L2 into two linear polarization components perpendicular to each other, and the photodetector 29 detects the strengths of the two linear polarization components by using two built-in PDs (photodiodes) to detect the magnetic rotation angle of the probe light L2 based on the ratio of the detected strengths. The OPM module 23 is further provided with a circuit board 30 and outputs the magnetic rotation angle of the probe light L2 detected for each crossing area 26A via the readout circuit 23C in the circuit board 30.

The output coil 24 is fixed in the magnetic shield 25 so as to face each crossing area 26A of the cell 26 of the OPM module 23 having the above-described configuration. With such a configuration, the magnetic signal BOUT generated by the output coil 24 based on the electromagnetic field BOUT detected by the receiving coil 22 is detected based on the magnetic rotation angle of the probe light L2 changing according to the inclination of the spin-polarized axis of the alkali metal atom. Herein, in the example of FIG. 2, the number of divisions of the crossing areas 26A is set to four, but the number of divisions may be changed to an arbitrary number. Further, the plurality of cells 26 may be provided in parallel, and the crossing areas 26A may be provided to be arranged two-dimensionally (for example, 4×4=16).

During the measurement of the brain magnetic field, the control device 5 determines currents for various coils based on the measured values output from the geomagnetic-correction magnetic sensor 2 and the active shield magnetic sensor 3 and outputs the control signal for outputting the currents to the coil power supply 6. The control device 5 determines the currents for the geomagnetic correction coil 7 and the geomagnetic gradient correction coil 8 so as to generate the magnetic field that cancels the magnetic field related to the geomagnetism based on the measured values of the plurality of geomagnetic-correction magnetic sensors 2. Further, the control device 5 determines the current for the fluctuating magnetic field correction coil 9 so as to generate the magnetic field that cancels the fluctuating magnetic field based on the measured values of the plurality of active shield magnetic sensors 3. The control device 5 outputs the control signal corresponding to the determined current to the coil power supply 6.

Specifically, the control device 5 determines the current for the geomagnetic correction coil 7 so that an average value of the measured values of the plurality of geomagnetic-correction magnetic sensors 2 is close to zero (as a result, so that the magnetic field in the opposite direction and having the same magnitude with respect to the geomagnetism at the position of the optically pumped magnetometer 1A is generated). The control device 5 outputs the control signal (static magnetic field correction control signal) corresponding to the determined current of the geomagnetic correction coil 7 to the coil power supply 6.

Further, the control device 5 determines the current for the geomagnetic gradient correction coil 8 so that a deviation from the average value of the measured values of the plurality of geomagnetic-correction magnetic sensors 2 is minimized (as a result, so that the magnetic field in the opposite direction and having the same magnitude with respect to the gradient magnetic field at the position of the optically pumped magnetometer 1A is generated). The control device 5 outputs the control signal (static magnetic field correction control signal) corresponding to the determined current of the geomagnetic gradient correction coil 8 to the coil power supply 6.

Furthermore, the control device 5 determines the current for the fluctuating magnetic field correction coil 9 so that the average value of the measured values of the plurality of active shield magnetic sensors 3 is close to zero (as a result, so that the magnetic field in the opposite direction and having the same magnitude with respect to the fluctuating magnetic field at the position of the optically pumped magnetometer 1A is generated). The control device 5 outputs the control signal (fluctuating magnetic field correction control signal) corresponding to the determined current of the fluctuating magnetic field correction coil 9 to the coil power supply 6.

Further, the control device 5 obtains information on the magnetism detected by the optically pumped magnetometer 1A by using the signal output from the amplifier 12A. When the optically pumped magnetometer 1A is the axial gradiometer, the control device 5 may remove the common mode noise by acquiring a difference between the output result in the measurement area and the output result in the reference area. In addition, the control device 5 may control operations such as irradiation timing and irradiation time of the pump laser 10 and the probe laser 11.

Further, during the measurement of the MR image, the control device 5 determines the current to be supplied to the geomagnetic correction coil 7 and the geomagnetic gradient correction coil 8 which operate as coils for applying the static magnetic field and the tilted magnetic field, respectively, and outputs the control signal for outputting the current to the coil power supply 6. That is, the control device 5 determines the current to flow through the geomagnetic correction coil 7 so as to apply the magnetic field as a static magnetic field having a predetermined strength (for example, 7 mT) in the X-axis direction to the head portion of the subject. Further, the control device 5 selectively determines a magnetic field gradient (dBx/dX) in the X-axis direction, a magnetic field gradient (dBx/dY) in the Y-axis direction, and a magnetic field gradient (dBx/dZ) in the Z-axis direction as a tilted magnetic field and determines the current to flow through the geomagnetic gradient correction coil 8. Accordingly, the position to be sliced in the MR image can be determined, and the position in a sliced plane can be encoded by phase encoding and frequency encoding. It is noted that, during the measurement of the MR image, the control device 5 outputs the control signal so as not to supply the current to the fluctuating magnetic field correction coil 9 that removes low-frequency noise.

Furthermore, during the measurement of the MR image, the control device 5 outputs the control signal for controlling the power to be supplied to the transmission coil 21 to the transmission coil controller 15 to control the transmission pulse having a predetermined frequency (for example, about 300 kHz when the strength of the static magnetic field is 7 mT) to irradiate the head portion of the subject with the transmission pulse. As a result, the protons of the sliced plane (the surface selected by the static magnetic field and the tilted magnetic field) resonate, and the spin is tilted. After that, the control device 5 controls the power of the transmission coil 21 to be turned off. Accordingly, the MR image can be acquired by measuring the state where the spin returns based on the output of the OPM module 23. More specifically, the control device 5 encodes the position by frequency and phase using a known spin echo sequence, a gradient echo sequence, or the like, measures the nuclear magnetic resonance signal from the proton, and converts the measurement result into the MR image by using an FFT.

The control device 5 is physically configured to include a memory such as a RAM and a ROM, a processor (arithmetic circuit) such as a CPU, a communication interface, and a storage unit such as a hard disk. Examples of the control device 5 include personal computers, cloud servers, smartphones, tablet terminals, and the like. The control device 5 functions by executing a program stored in the memory on the CPU of a computer system.

The coil power supply 6 outputs a predetermined current to each of the geomagnetic correction coil 7, the geomagnetic gradient correction coil 8, and the fluctuating magnetic field correction coil 9 according to the control signal output from the control device 5. Specifically, the coil power supply 6 outputs the current to the geomagnetic correction coil 7 according to the control signal related to the geomagnetic correction coil 7. The coil power supply 6 outputs the current to the geomagnetic gradient correction coil 8 according to the control signal related to the geomagnetic gradient correction coil 8. The coil power supply 6 outputs the current to the fluctuating magnetic field correction coil 9 according to the control signal related to the fluctuating magnetic field correction coil 9.

The transmission coil controller 15 is electrically connected to the transmission coil 21 and supplies the power to the transmission coil 21 so as to perform the irradiation with the transmission pulse having the predetermined frequency according to the control signal output from the control device 5.

The geomagnetic correction coil 7 is a coil for correcting the magnetic field of the geomagnetism among the magnetic fields related to the geomagnetism at the position of the optically pumped magnetometer 1A. The geomagnetic correction coil 7 generates the magnetic field according to the current supplied from the coil power supply 6 to perform cancelling of the geomagnetism. The geomagnetic correction coil 7 has, for example, a pair of geomagnetic correction coils 7A and 7B. The pair of geomagnetic correction coils 7A and 7B are arranged so as to interpose the optically pumped magnetometer 1A (for example, to the left and right of the subject). The pair of geomagnetic correction coils 7A and 7B generate the magnetic field in the opposite direction and having the same magnitude with respect to the geomagnetism at the position of the optically pumped magnetometer 1A according to the current supplied from the coil power supply 6. The direction of the magnetic field is, for example, the X-axis direction, the Y-axis direction, and the Z-axis direction. The geomagnetism at the position of the optically pumped magnetometer 1A is canceled by the magnetic field in the opposite direction and having the same magnitude generated by the geomagnetic correction coil 7. In this manner, the geomagnetic correction coil 7 corrects the geomagnetism at the position of the optically pumped magnetometer 1A.

Further, the geomagnetic correction coil 7 has a role as a static magnetic field coil for generating the static magnetic field in the X-axis direction during the measurement of the MR image. The geomagnetic correction coil 7 generates the static magnetic field having a predetermined strength according to the current supplied from the coil power supply 6.

The geomagnetic gradient correction coil 8 is a coil for correcting the gradient magnetic field among the magnetic fields related to the geomagnetism at the position of the optically pumped magnetometer 1A. The geomagnetic gradient correction coil 8 generates the magnetic field according to the current supplied from the coil power supply 6 to perform cancelling of the gradient magnetic field. The geomagnetic gradient correction coil 8 has, for example, a pair of geomagnetic gradient correction coils 8A and 8B. The pair of geomagnetic gradient correction coils 8A and 8B are arranged so as to interpose the optically pumped magnetometer 1A (for example, to the left and right of the subject). The pair of geomagnetic gradient correction coils 8A and 8B generate the magnetic field in the opposite direction and having the same magnitude with respect to the gradient magnetic field at the position of the optically pumped magnetometer 1A according to the current supplied from the coil power supply 6. The direction of the magnetic field is, for example, the X-axis direction, the Y-axis direction, and the Z-axis direction. The gradient magnetic field at the position of the optically pumped magnetometer 1A is canceled by the magnetic field in the opposite direction and having the same magnitude generated by the geomagnetic gradient correction coil 8. In this manner, the geomagnetic gradient correction coil 8 corrects the gradient magnetic field at the position of the optically pumped magnetometer 1A.

Further, the geomagnetic gradient correction coil 8 has a role as a gradient magnetic field coil for generating the tilted magnetic field during the measurement of the MR image. The geomagnetic gradient correction coil 8 generates the tilted magnetic field having the selective gradient in the X-axis direction, the Y-axis direction, and the Z-axis direction according to the current supplied from the coil power supply 6.

The fluctuating magnetic field correction coil 9 is a coil for correcting the fluctuating magnetic field at the position of the optically pumped magnetometer 1A. The fluctuating magnetic field correction coil 9 generates the magnetic field according to the current supplied from the coil power supply 6 to perform cancelling of the fluctuating magnetic field. The fluctuating magnetic field correction coil 9 has, for example, a pair of fluctuating magnetic field correction coils 9A and 9B. The pair of fluctuating magnetic field correction coils 9A and 9B are arranged so as to interpose the optically pumped magnetometer 1A (for example, to the left and right of the subject). The pair of fluctuating magnetic field correction coils 9A and 9B generate the magnetic field in the opposite direction and having the same magnitude with respect to the fluctuating magnetic field at the position of the optically pumped magnetometer 1A according to the current supplied from the coil power supply 6. The direction of the magnetic field is, for example, the X-axis direction, the Y-axis direction, and the Z-axis direction. The fluctuating magnetic field at the position of the optically pumped magnetometer 1A is canceled by the magnetic field in the opposite direction and having the same magnitude generated by the fluctuating magnetic field correction coil 9. In this manner, the fluctuating magnetic field correction coil 9 corrects the fluctuating magnetic field at the position of the optically pumped magnetometer 1A.

The pump laser 10 is a laser device that generates the pump light. The pump light emitted from the pump laser 10 is incident on each of the plurality of optically pumped magnetometers 1A and the plurality of optically pumped magnetometers 23A by fiber branching.

The probe laser 11 is a laser device that generates probe light. The probe light emitted from the probe laser 11 is incident on each of the plurality of optically pumped magnetometers 1A and the optically pumped magnetometers 23A by fiber branching.

The amplifier 12A is a device or circuit that amplifies a signal of the output result from the OPM module 1 (specifically, the readout circuit 1C) and outputs the signal to the control device 5.

The amplifier 12B is a device or circuit that amplifies a signal of the output result from the OPM module 23 (specifically, the readout circuit 23C) and outputs the signal to the control device 5.

The heater controller 13 is a temperature control device connected to the heater for heating the cell of the optically pumped magnetometer 1A and the cell of the optically pumped magnetometer 23A and a thermocouple (not illustrated) for measuring the temperature of each cell. The heater controller 13 receives temperature information of the cell from the thermocouple and adjusts the heating of the heater based on the temperature information to adjust the temperature of the cell.

The electromagnetic shield 14 is a shield member that shields electromagnetic noise having a high frequency (for example, 10 kHz or more) and is configured with, for example, a mesh woven with metal threads, a non-magnetic metal plate such as aluminum, or the like. The electromagnetic shield 14 is arranged so as to surround the OPM module 1 or 23, the transmission coil 21, the receiving coil 22, the output coil 24, the geomagnetic-correction magnetic sensor 2, the active shield magnetic sensor 3, the non-magnetic frame 4, the geomagnetic correction coil 7, and the geomagnetic gradient correction coil 8, and the fluctuating magnetic field correction coil 9. During the measurement of the MR image, the electromagnetic shield 14 can prevent noise in the 300 kHz band which is the measurement frequency from entering the receiving coil 22 and increasing the noise. Further, it is possible to prevent the operation from becoming unstable due to high-frequency noise incident on the optically pumped magnetometer 1A during the measurement of the brain magnetic field.

[Brain Measurement Method Performed by Brain Measurement System (Brain Measurement Operation)]

Figure 3:
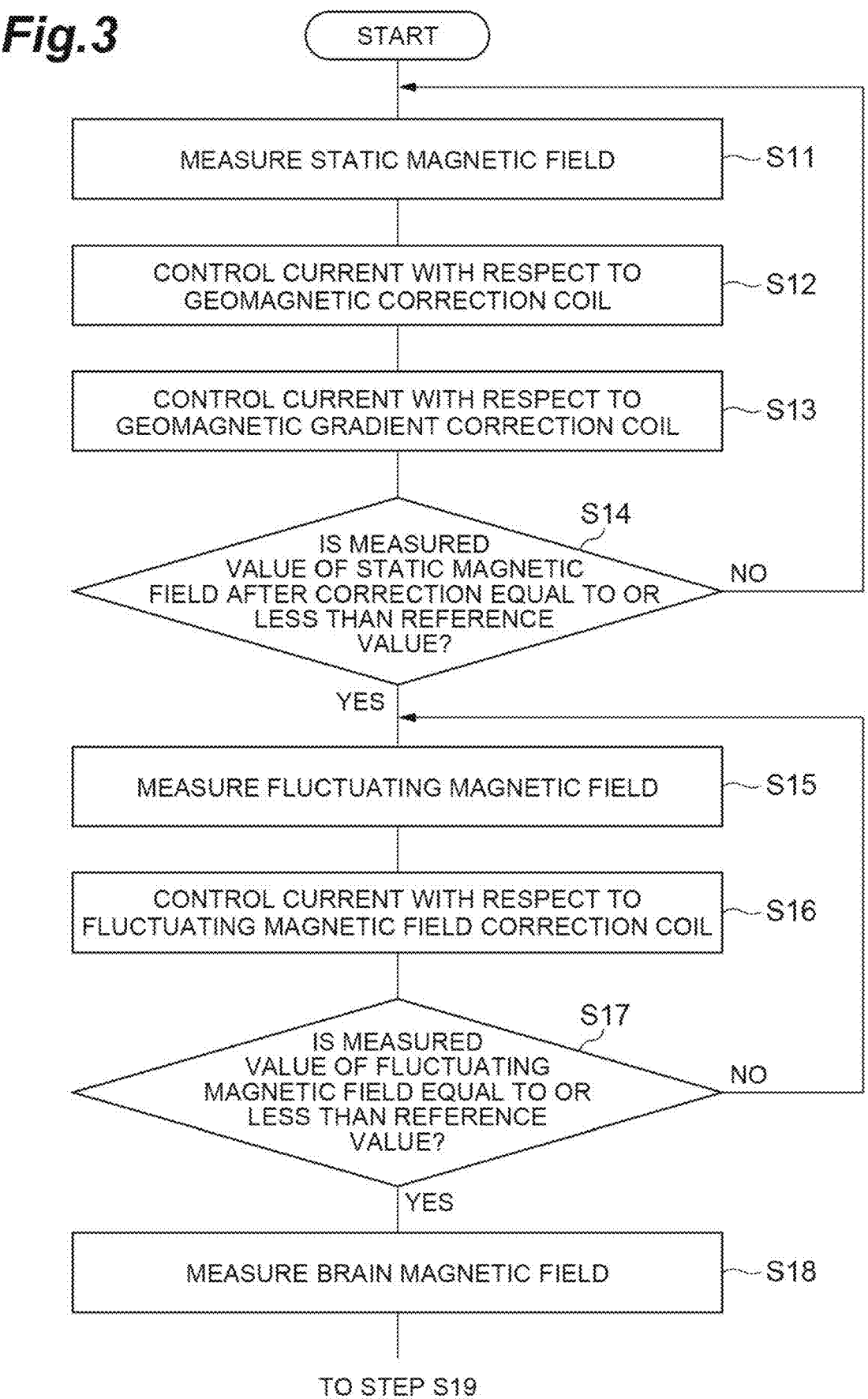
FIG. 3 is a flowchart illustrating operations of the brain measurement system according to the embodiment.
Figure 4:
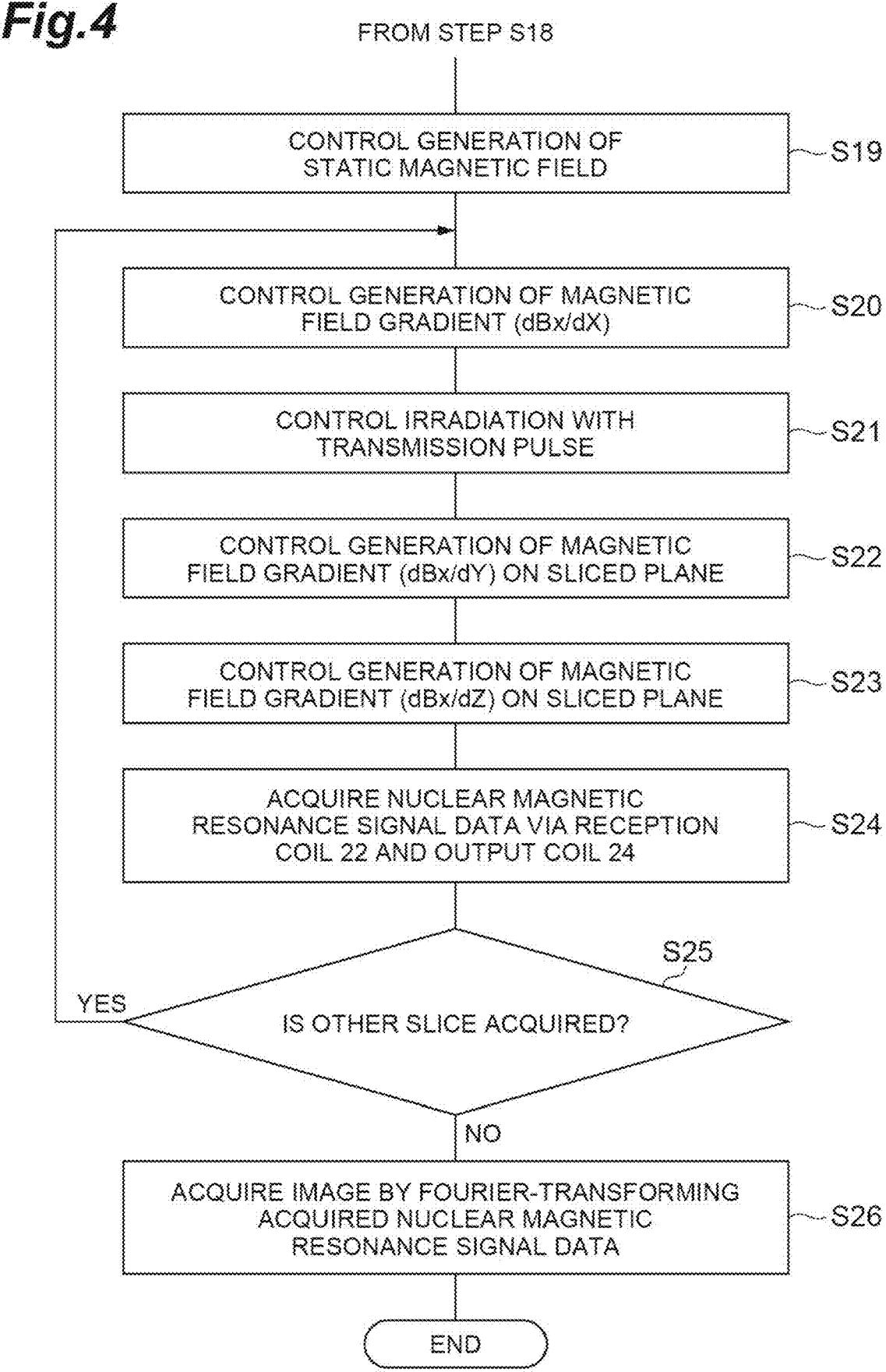
FIG. 4 is a flowchart illustrating the operations of the brain measurement system according to the embodiment.

Next, a brain measurement method using the brain measurement system M1 according to the embodiment will be described with reference to FIGS. 3 and 4. FIGS. 3 and 4 are flowcharts illustrating operations of the brain measurement system M1.

First, when the measurement of the brain magnetic field is started with the non-magnetic frame 4 attached to the subject, the geomagnetic-correction magnetic sensor 2 measures the magnetic field related to the geomagnetism, which is the static magnetic field (step S11). The geomagnetic-correction magnetic sensor 2 measures the geomagnetism and the gradient magnetic field at each position of the optically pumped magnetometer 1A and outputs the measured value to the control device 5.

The control device 5 and the coil power supply 6 control the current with respect to the geomagnetic correction coil 7 (step S12). The control device 5 determines the current for the geomagnetic correction coil 7 so that the magnetic field in the opposite direction and having the same magnitude with respect to the geomagnetism at the position of the optically pumped magnetometer 1A is generated based on the measured value of the geomagnetic-correction magnetic sensor 2. More specifically, the control device 5 determines the current for the geomagnetic correction coil 7 so that, for example, the average value of the measured values of the plurality of geomagnetic-correction magnetic sensors 2 is close to zero. The control device 5 outputs the control signal corresponding to the determined current to the coil power supply 6. The coil power supply 6 outputs a predetermined current to the geomagnetic correction coil 7 according to the control signal output by the control device 5. The geomagnetic correction coil 7 generates the magnetic field according to the current supplied from the coil power supply 6. The geomagnetism at the position of the optically pumped magnetometer 1A is canceled by the magnetic field in the opposite direction and having the same magnitude generated by the geomagnetic correction coil 7.

The control device 5 and the coil power supply 6 control the current with respect to the geomagnetic gradient correction coil 8 (step S13). The control device 5 determines the current for the geomagnetic gradient correction coil 8 so that the magnetic field in the opposite direction and having the same magnitude with respect to the gradient magnetic field at the position of the optically pumped magnetometer 1A is generated based on the measured value of the geomagnetic-correction magnetic sensor 2. More specifically, the control device 5 determines the current for the geomagnetic gradient correction coil 8 so that, for example, a deviation from the average value of the measured values of the plurality of geomagnetic-correction magnetic sensors 2 is minimized. The control device 5 outputs the control signal corresponding to the determined current to the coil power supply 6. The coil power supply 6 outputs the predetermined current to the geomagnetic gradient correction coil 8 according to the control signal output by the control device 5. The geomagnetic gradient correction coil 8 generates the magnetic field according to the current supplied from the coil power supply 6. The gradient magnetic field at the position of the optically pumped magnetometer 1A is canceled by the magnetic field in the opposite direction and having the same magnitude generated by the geomagnetic gradient correction coil 8.

The control device 5 determines whether or not the measured value of the static magnetic field after the correction (magnetic field related to the geomagnetism) is equal to or less than a reference value (step S14). The measured value of the static magnetic field after the correction is a value measured by the geomagnetic-correction magnetic sensor 2 after the static magnetic field is corrected by the geomagnetic correction coil 7 and the geomagnetic gradient correction coil 8. The reference value is the magnitude of the magnetic field in which the optically pumped magnetometer 1A normally operates and can be, for example, 1 nT. When the measured value of the static magnetic field is not equal to or less than the reference value ("NO" in step S14), the process returns to step S11. When the measured value of the static magnetic field is equal to or less than the reference value ("YES" in step S14), the process proceeds to step S15.

The active shield magnetic sensor 3 measures the fluctuating magnetic field (step S15). The active shield magnetic sensor 3 measures the fluctuating magnetic field at each position of the optically pumped magnetometer 1A and outputs the measured value to the control device 5.

The control device 5 and the coil power supply 6 control the current with respect to the fluctuating magnetic field correction coil 9 (step S16). The control device 5 determines the current for the fluctuating magnetic field correction coil 9 so that the magnetic field in the opposite direction and having the same magnitude with respect to the fluctuating magnetic field at the position of the optically pumped magnetometer 1A is generated based on the measured value of the active shield magnetic sensor 3. More specifically, the control device 5 determines the current for the fluctuating magnetic field correction coil 9 so that, for example, the average value of the measured values of the plurality of active shield magnetic sensors 3 is close to zero. The control device 5 outputs the control signal corresponding to the determined current to the coil power supply 6. The coil power supply 6 outputs the predetermined current to the fluctuating magnetic field correction coil 9 according to the control signal output by the control device 5. The fluctuating magnetic field correction coil 9 generates the magnetic field according to the current supplied from the coil power supply 6. The fluctuating magnetic field at the position of the optically pumped magnetometer 1A is canceled by the magnetic field in the opposite direction and having the same magnitude generated by the fluctuating magnetic field correction coil 9.

The control device 5 determines whether or not the measured value of the fluctuating magnetic field after the correction is equal to or less than the reference value (step S17). The measured value of the fluctuating magnetic field after the correction is a value measured by the active shield magnetic sensor 3 after the fluctuating magnetic field is corrected by the fluctuating magnetic field correction coil 9. The reference value is a noise level at which the brain magnetic field can be measured and can be set to, for example, 1 pT. When the measured value of the fluctuating magnetic field is not equal to or less than the reference value ("NO" in step S17), the process returns to step S15. When the measured value of the fluctuating magnetic field is equal to or less than the reference value ("YES" in step S17), the process proceeds to step S18.

The optically pumped magnetometer 1A measures the brain magnetic field (step S18). The control device 5 outputs the acquired measurement result to a predetermined output destination. The predetermined output destination may be a memory of the control device 5, a storage device such as a hard disk, an output device such as a display, or an external device such as a terminal device connected via a communication interface. Since the static magnetic field (magnetic field related to geomagnetism) and the fluctuating magnetic field at the position of the optically pumped magnetometer 1A have been canceled so as to be equal to or less than the predetermined reference value, the optically pumped magnetometer 1A can measure the brain magnetic field in a state where the influence of the static magnetic field (magnetic field related to geomagnetism) and the influence of the fluctuating magnetic field are avoided.

Moving to FIG. 4, when the measurement of the MR image is continuously started in a state where the non-magnetic frame 4 is attached to the subject, the control device 5 determines the current to be supplied to the geomagnetic correction coil 7 for applying the static magnetic field and outputs the control signal to the coil power supply 6 to control the generation of the static magnetic field on the head portion of the subject in the X-axis direction (step S19). Next, the control device 5 determines the current to be supplied to the geomagnetic gradient correction coil 8 for generating the tilted magnetic field and outputs the control signal to the coil power supply 6 to control the generation of the magnetic field gradient (dBx/dX) in the X-axis direction (step S20). At the same time, the control device 5 outputs the control signal for controlling the power supplied to the transmission coil 21 to the transmission coil controller 15 to control the transmission pulse to irradiate the head portion of the subject with the transmission pulse (step S21). Accordingly, the protons on the predetermined sliced plane are excited.

Furthermore, the control device 5 determines the current to be supplied to the geomagnetic gradient correction coil 8 for generating the tilted magnetic field and outputs the control signal to the coil power supply 6 to control the generation of the magnetic field gradient (dBx/dY) on the sliced plane in the Y-axis direction (step S22). Accordingly, phase encoding is performed. Then, the control device 5 determines the current to be supplied to the geomagnetic gradient correction coil 8 for generating the tilted magnetic field and outputs the control signal to the coil power supply 6 to control the generation of the magnetic field gradient (dBx/dZ) on the sliced plane in the Z-axis direction (step S23). Accordingly, frequency encoding is performed.

At the same time, the nuclear magnetic resonance signal from the proton is output from the OPM module 23 via the receiving coil 22 and the output coil 24, and thus, the control device 5 acquires the data of the nuclear magnetic resonance signal (step S24). After that, the control device 5 determines whether or not to acquire the nuclear magnetic resonance signal data related to the other sliced plane (step S25). As a result of the determination, when the nuclear magnetic resonance signal data related to the other sliced plane is acquired ("YES" in step S25), the process returns to step S20. On the other hand, when the nuclear magnetic resonance signal data related to the other sliced plane is not acquired ("NO" in step S25), the MR image is acquired by Fourier-transforming the nuclear magnetic resonance signal data acquired so far (step S26). The control device 5 outputs the acquired MR image to the predetermined output destination. The predetermined output destination may be a memory of the control device 5, a storage device such as a hard disk, an output device such as a display, or an external device such as a terminal device connected via a communication interface.

[Configuration of Resonance Adjustment Circuit]

As described above, the brain measurement system M1 includes the resonance adjustment circuit 50 (refer to FIG. 1) as a configuration included in the MRI module. Hereinafter, the details of the configuration of the resonance adjustment circuit 50 will be described. First, the purpose of providing the resonance adjustment circuit 50 will be described with reference to FIGS. 5 and 6.

Figure 5B:
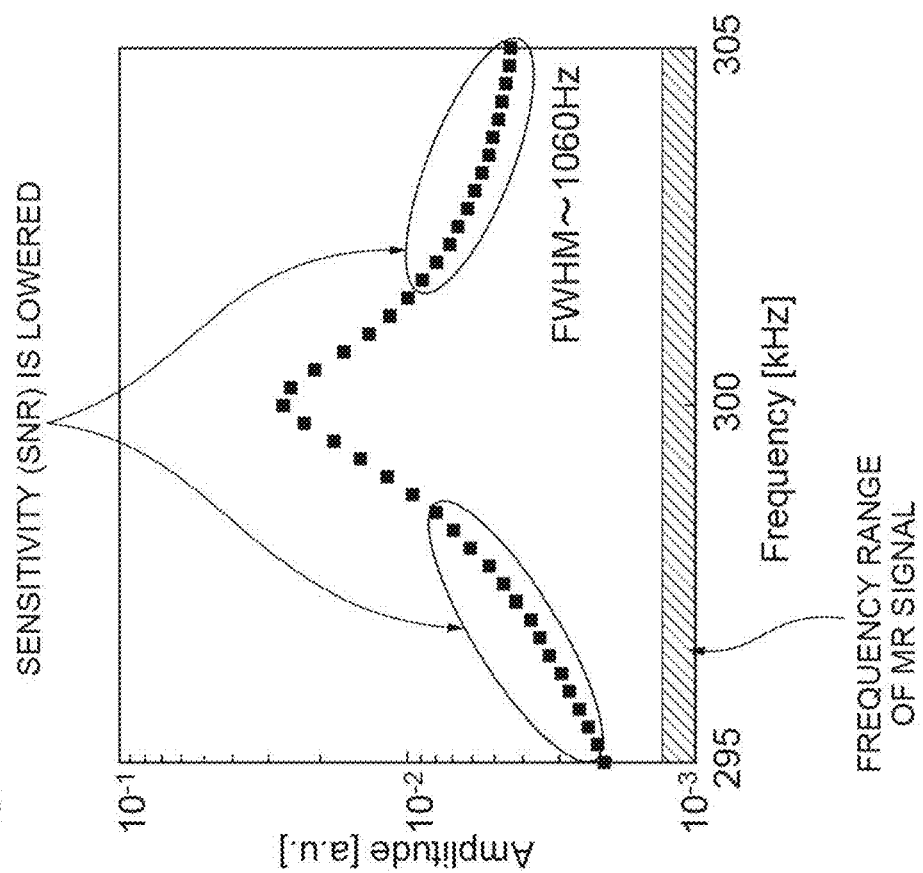
FIGS. 5A and 5B are diagrams illustrating an example of a detection sensitivity corresponding to a detection band.
Figure 5A:
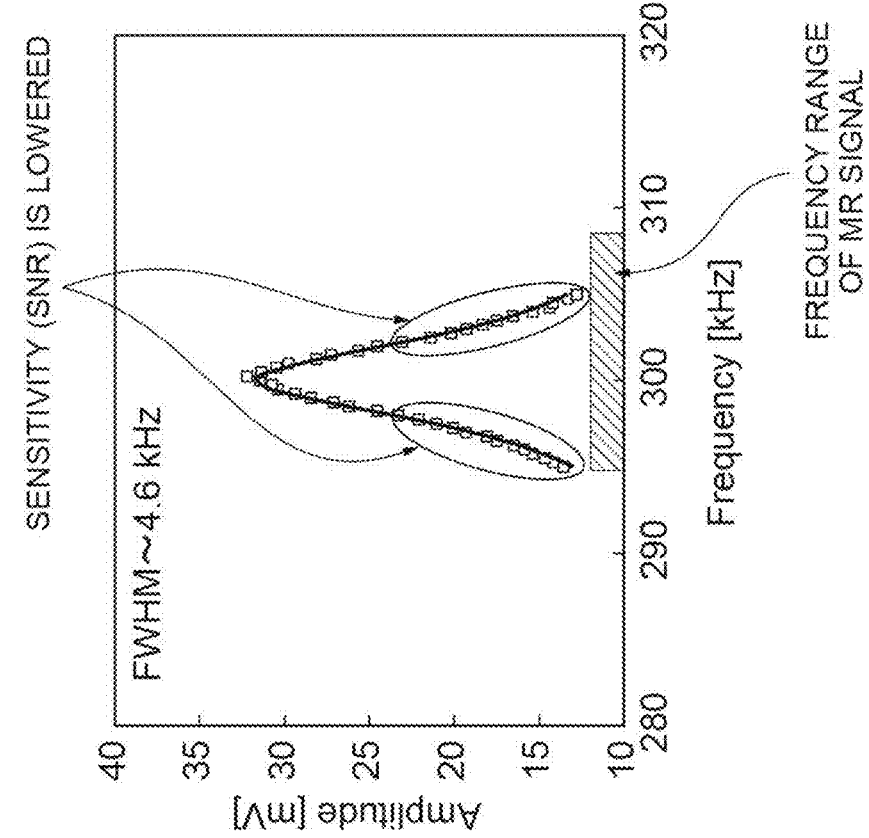

FIGS. 5A and 5B are diagrams illustrating examples of the detection sensitivity corresponding to the detection band. As described above, the brain measurement system M1 may adopt the OPM module 23 as a detection unit or may adopt an amplifier (not illustrated) as an alternative to the OPM module 23. FIG. 5A illustrates an example of the detection sensitivity corresponding to the detection band when the amplifier (not illustrated) is used as a detection unit. FIG. 5B illustrates an example of the detection sensitivity corresponding to the detection band when the OPM module 23 is adopted as a detection unit. In FIGS. 5A and 5B, the horizontal axis represents a frequency (detection band), and the vertical axis represents an amplitude (detection sensitivity). In FIG. 5A, the amplitude is indicated by an absolute value (mV), and in FIG. 5B, the amplitude is indicated by a.u. In addition, the frequency range of the MR signal (nuclear magnetic resonance signal) illustrated in FIGS. 5A and 5B is a range specified by frequency encoding.

Now, in the example illustrated in FIG. 5A in which the amplifier (not illustrated) is adopted as a detection unit, there is a frequency area in which the sensitivity (SNR) is significantly reduced in a frequency range of the MR signal. The FWHM which is a spectral width of the portion where the sensitivity is 50% of the peak value becomes about 4.6 kHz. Further, even in the example in which the OPM module 23 is adopted as a detection unit illustrated in FIG. 5B, there is a frequency area in which the sensitivity (SNR) is significantly reduced in the frequency range of the MR signal, and the FWHM becomes about 1060 Hz. As described above, in the detection unit, there is a frequency area in which the sensitivity is not sufficient in the frequency range of the MR signal.

Figure 6:
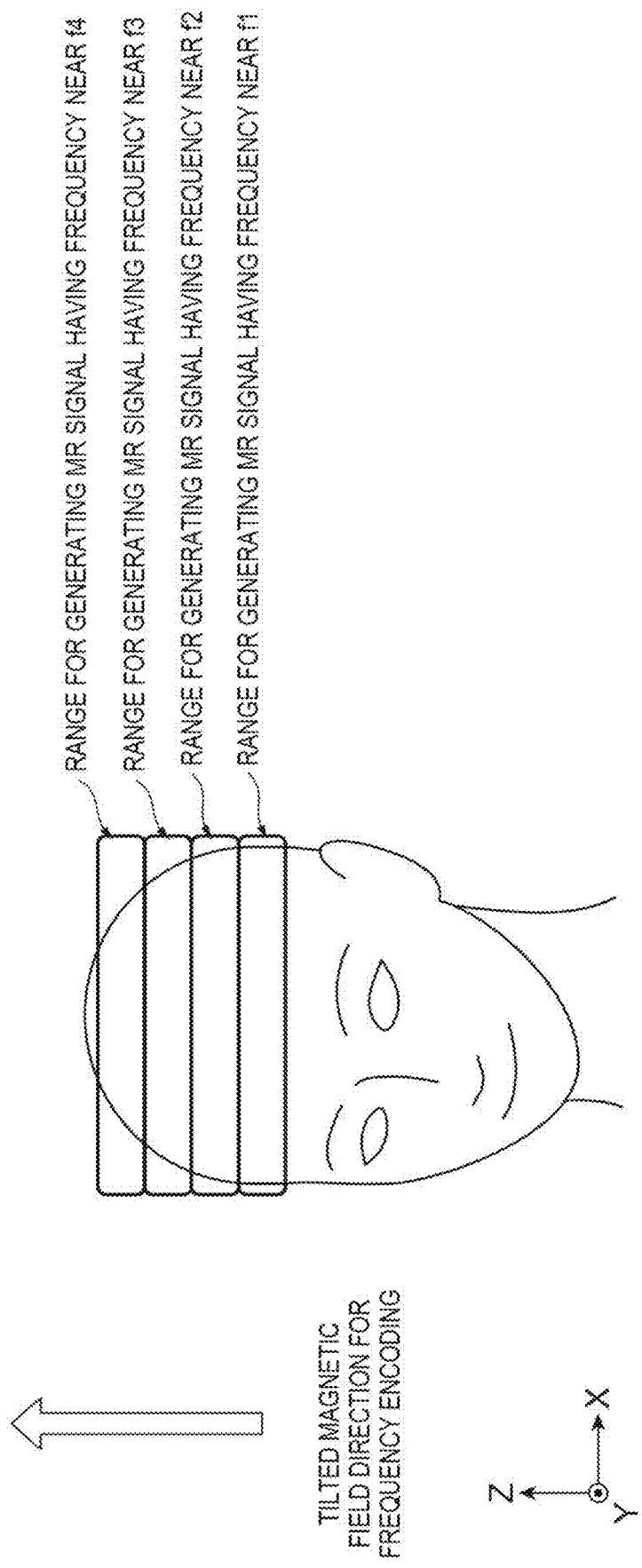
FIG. 6 is a diagram illustrating a frequency-encoded MR signal.

FIG. 6 is a diagram illustrating a frequency-encoded MR signal. As illustrated in FIG. 6, by supplying the current to the geomagnetic gradient correction coil 8 for generating the tilted magnetic field, the magnetic field gradient (dBx/dZ) in the Z-axis direction is generated, and frequency encoding is performed. When frequency encoding is performed, the frequency band of the generated MR signal is determined according to the position on the head portion in the Z-axis direction. That is, as illustrated in FIG. 6, for example, the lowest side of the head portion becomes a range for generating the MR signal having a frequency near f1, the upper side of the range becomes a range for generating the MR signal having a frequency near f2 (f2>f1), the upper side of the range becomes a range for generating the MR signal having a frequency near f3 (f3>f2), and the upper side of the range becomes a range for generating the MR signal having a frequency near f4 (f4>f3). In this manner, when the generated magnetic field gradient in the Z-axis direction and the position of the head portion are determined, since the frequency band of the generated MR signal can be specified, by providing the resonance adjustment circuit 50 for extracting the signal of the specific frequency band (resonance frequency) for each position (area), the frequency range of the MR signal can be detected with high sensitivity without omission. Hereinafter, the specific configuration example of the resonance adjustment circuit 50 will be described with reference to FIGS. 7 to 10.

Figure 7:
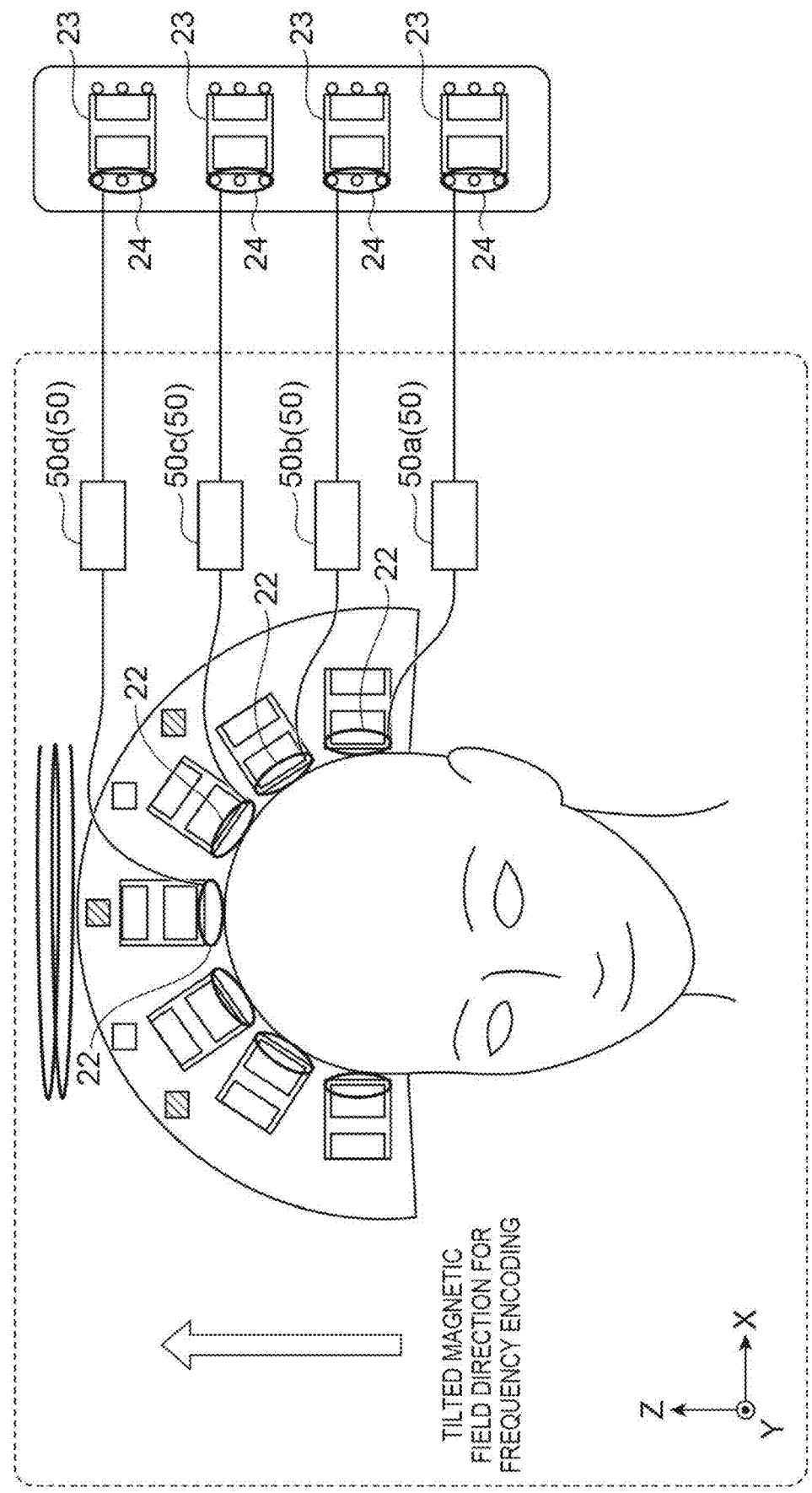
FIG. 7 is a schematic view illustrating a portion of a brain measurement system including a resonance adjustment circuit.

FIG. 7 is a schematic view illustrating a portion of the brain measurement system M1 including the plurality of resonance adjustment circuits 50. The plurality of resonance adjustment circuits 50 are provided corresponding to each of the plurality of receiving coils 22 and are circuits for extracting and outputting the signal having the predetermined resonance frequency of the current output from the receiving coil 22. In FIG. 7, resonance adjustment circuits 50a, 50b, 50c, and 50d are exemplified as a plurality of resonance adjustment circuits 50. In addition, although the resonance adjustment circuits 50 are provided, for example, in a one-to-one correspondence with the respective receiving coils 22, only a portion of the resonance adjustment circuits 50 is illustrated in FIG. 7, and only four resonance adjustment circuits 50a, 50b, 50c, and 50d are illustrated.

The resonance frequency related to each of the plurality of resonance adjustment circuits 50 is set according to the position of the corresponding receiving coil 22 in the Z-axis direction and the magnetic field gradient in the Z-axis direction generated by controlling the tilted magnetic field. As described above, when frequency encoding is performed by controlling the tilted magnetic field, the frequency band of the MR signal changes along the Z-axis direction (refer to FIG. 6). For this reason, by setting the resonance frequency of the resonance adjustment circuit 50 in consideration of the position of the receiving coil 22 in the Z-axis direction and the magnetic field gradient, the MR signal output from the receiving coil 22 can be suitably extracted, and the MR signal can be detected with high sensitivity in the OPM module 23 in the subsequent stage. In addition, the receiving coil 22 has a diameter of about 30 to 50 mm and is arranged so as to surround the head portion. With respect to the receiving coils 22 arranged at the same height in the Z-axis direction, the resonance frequency becomes the same in the resonance adjustment circuit 50. For example, the resonance frequency related to the receiving coil 22 at the center position of the head portion is set to 300 kHz, and the resonance frequency is shifted by 1.5 kHz every shifting by 30 mm in the Z direction. Accordingly, the MR signals emitted from the brain near each receiving coil 22 can be efficiently detected. The receiving coil 22 having a diameter of about 30 to 50 mm has high sensitivity for capturing MR signals generated in the vicinity of the coil while the receiving coil 22 has low sensitivity for noise generated at the position far from the coil. For this reason, by arranging the large number of such receiving coils 22, the SNR of the MR image can be improved.

As illustrated in FIG. 7, the OPM modules 23 which are a plurality of detection units are provided corresponding to each of the plurality of resonance adjustment circuits 50 (resonance adjustment circuits 50a, 50b, 50c, and 50d in FIG. 7) to detect the signal having the resonance frequency output from the resonance adjustment circuits 50. The frequency band in which the detection sensitivity of the OPM modules 23 is maximized includes the resonance frequency related to the corresponding resonance adjustment circuits 50. The output coil 24 is fixed so as to face the OPM module 23. Each OPM module 23 may be provided in a one-to-one correspondence with the resonance adjustment circuit 50 as illustrated in FIG. 7.

Alternatively, the plurality of OPM modules 23 may include one OPM module 23 that detects all the signals related to the two or more receiving coils 22 having the same resonance frequency related to the resonance adjustment circuit 50 by adjusting the phases of the signals. As described above, the resonance frequency of each resonance adjustment circuit 50 is determined in consideration of the position of the corresponding receiving coil 22 in the Z-axis direction. For this reason, the resonance adjustment circuits 50 can be rephrased as the two or more resonance adjustment circuits 50 having the same resonance frequency, that is, the two or more resonance adjustment circuits 50 in which the positions of the corresponding receiving coils 22 in the Z-axis direction are the same (or approximate) with each other. There is a concern that, when the signals related to the two or more receiving coils 22 are simply detected by one OPM module 23, the signals may cancel each other because the phases of the signals are different from each other. For this reason, when the signals related to the two or more receiving coils 22 are detected by one OPM module 23, the phases of the signals are adjusted and detected so that the signals do not cancel each other.

Figure 8:
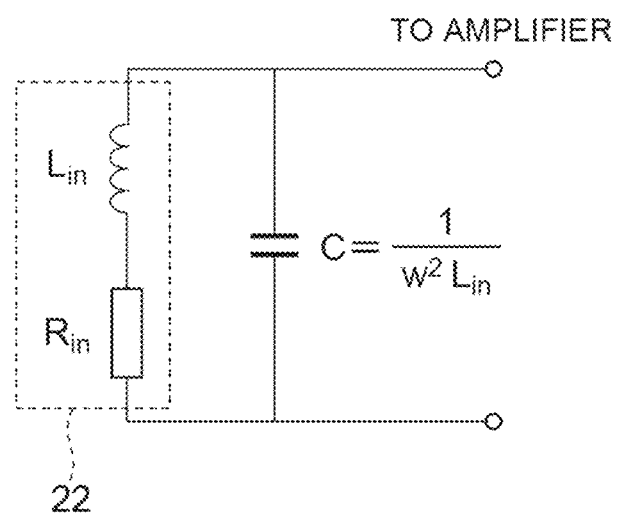
FIG. 8 is a diagram illustrating an example of a configuration of the resonance adjustment circuit.
Figure 9:
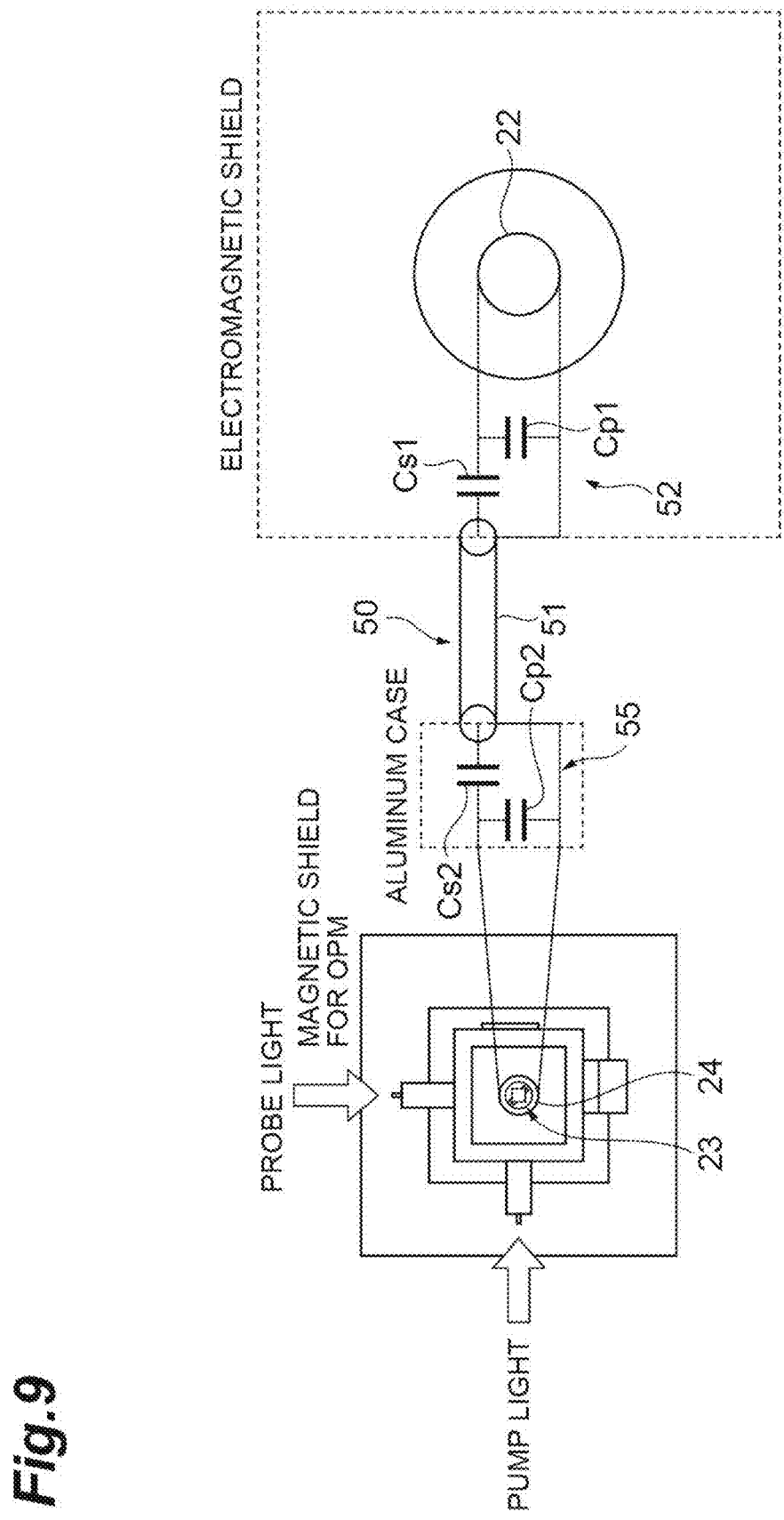
FIG. 9 is a diagram illustrating an example of the configuration of the resonance adjustment circuit.

FIGS. 8 and 9 are views illustrating the examples of the configuration of the resonance adjustment circuit 50. FIG. 8 illustrates an example of the resonance adjustment circuit 50 in the case where the amplifier (not illustrated) is adopted as a detection unit, and specifically, illustrates a parallel resonance circuit in which a capacitor C is connected in parallel to the receiving coil 22 in which a resistor Rin and an inductor Lin are connected in series. In such a parallel resonant circuit, for example, under the condition that the resistance Rin=0.64Ω and the inductance Lin=105 pH, the value of the capacitor C is set to be a predetermined resonance frequency (for example, 300 kHz) from the equation of $C=1/\omega^2 Lin$.

FIG. 9 illustrates an example of the resonance adjustment circuit 50 when the OPM module 23 is adopted as a detection unit. The resonance adjustment circuit 50 illustrated in FIG. 9 includes an input side circuit 52 in which capacitors Cs1 and Cp1 are provided in series and parallel to the receiving coil 22, an output side circuit 55 in which capacitors Cs2 and Cp2 are provided in series and parallel to the output coil 24, and a coaxial cable 51 connecting the input side circuit 52 and the output side circuit 55. In the configuration illustrated in FIG. 9, the receiving coil 22 and the input side circuit 52 are surrounded by the same electromagnetic shield, the output side circuit 55 is surrounded by an aluminum case, and the output coil 24 and the OPM module 23 are surrounded by a magnetic shield for OPM.

Figure 10:
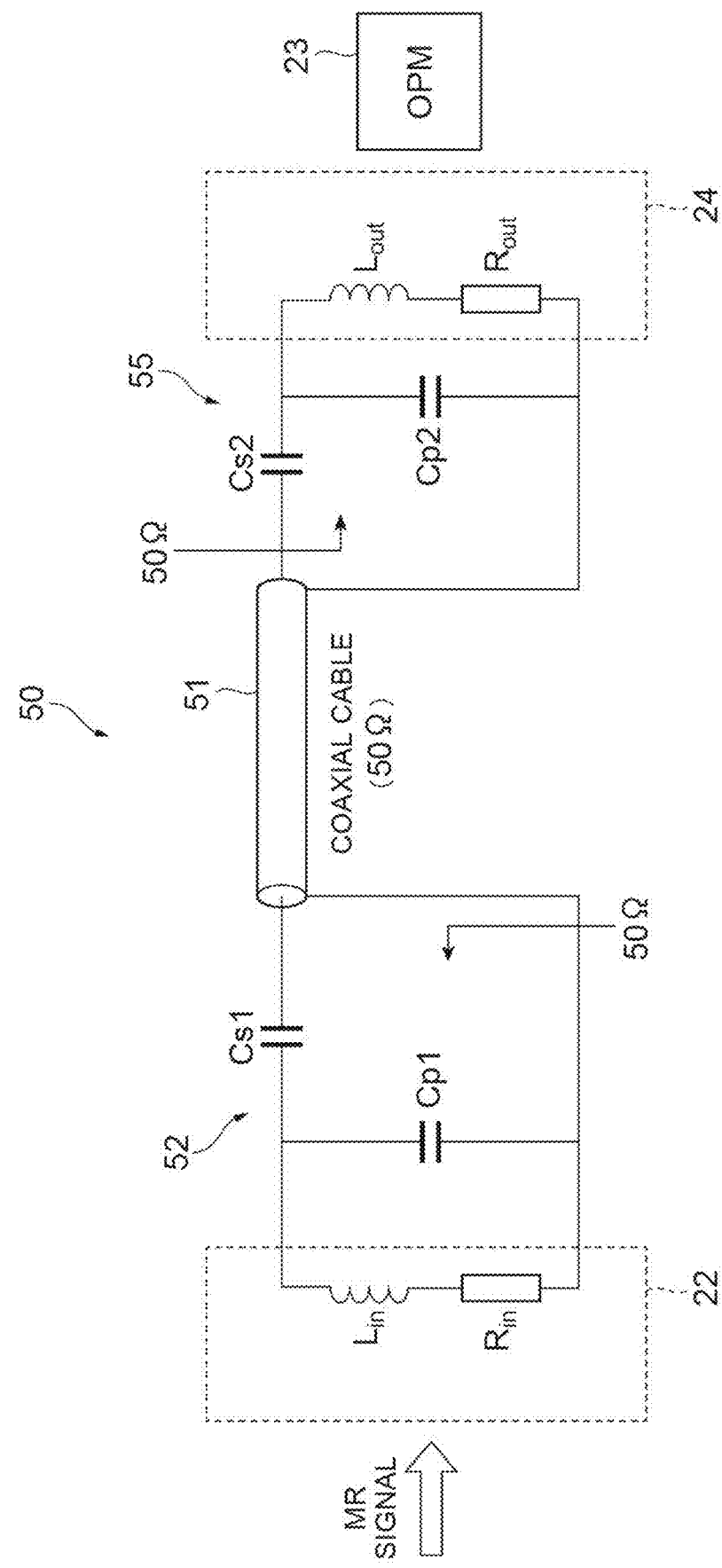
FIG. 10 is a diagram illustrating a detailed circuit configuration of the resonance adjustment circuit illustrated in FIG. 9.

FIG. 10 is a diagram illustrating a detailed circuit configuration of the resonance adjustment circuit illustrated in FIG. 9. As illustrated in FIG. 10, in the receiving coil 22, the resistor Rin and the inductor Lin are connected in series. Further, in the output coil 24, a resistor Rout and an inductor Lout are connected in series. Then, as described above, the resonance adjustment circuit 50 includes the input side circuit 52 in which the capacitors Cs1 and Cp1 are provided in series and parallel to the receiving coil 22, the output side circuit 55 in which the capacitors Cs2 and Cp2 are provided in series and parallel to the output coil 24, and the coaxial cable 51 connecting the input side circuit 52 and the output side circuit 55.

In such a resonance adjustment circuit 50, the capacitances of the capacitors Cs1 and Cp1 of the input side circuit 52 are adjusted so that the input impedance which is impedance when the input side circuit 52 and the receiving coil 22 side are viewed from the coaxial cable 51 becomes the same as the impedance of the coaxial cable 51 at the resonance frequency. Further, in the resonance adjustment circuit 50, the capacitances of the capacitors Cs2 and Cp2 of the output side circuit 55 are adjusted so that the output impedance which is impedance when the output side circuit 55 and the output coil 24 side are viewed from the coaxial cable 51 becomes the same as the impedance of the coaxial cable 51 at the resonance frequency. In this manner, by adjusting the capacitances of the capacitors Cs1 and Cp1 of the input side circuit 52 and the capacitances of the capacitors Cs2 and Cp2 of the output side circuit 55, both the input impedance and the output impedance viewed from the coaxial cable 51 become the same as the impedance of the coaxial cable 51 at the resonance frequency, so that the signal reflection of the signal component of the resonance frequency can be suppressed. It is noted that the impedance of the coaxial cable 51 is, for example, 50Ω.

In the configuration illustrated in FIG. 10, specifically, the capacitances of the capacitors Cs1 and Cp1 of the input side circuit 52 are obtained so as to satisfy the following equations (1) and (2). 50 on the right side of the equation (1) indicates the impedance of the coaxial cable 51. ω indicates an angular frequency and is obtained from the resonance frequency. It is noted that the capacitances of the capacitors Cs2 and Cp2 of the output side circuit 55 are also obtained based on the same equation.

$$Z + 1/j\omega Cs1 = 50 \quad (1)$$

$$Z = (1/j\omega Cp1) // (Rin + j\omega Lin) \quad (2)$$

Now, assuming that, for example, Lin=105.7 μH, Rin=0.77Ω, LOUT=3.0 μH, ROUT=0.18Ω, and resonance frequency=300 kHz, it is obtained that Cp1=2.3 nF, Cs1=330 pF, Cp2=89 nF, and Cs2=6.6 nF by the above equations (1) and (2).

Next, the functions and effects of the brain measurement system M1 according to the embodiment will be described. The brain measurement system M1 according to the embodiment is provided with the resonance adjustment circuit 50 that extracts the signal having the predetermined resonance frequency of the current output from the receiving coil 22. Then, the resonance frequency of each of the plurality of resonance adjustment circuits 50 is set according to the position of the corresponding receiving coil 22 in the Z-axis direction and the magnetic field gradient in the Z-axis direction. In this manner, by setting the resonance frequency of the resonance adjustment circuit 50 in consideration of the position of the corresponding receiving coil 22 and the generated magnetic field gradient, the sensitivity of the signal detected in the OPM module 23 provided corresponding to the resonance adjustment circuit 50 can be improved. Herein, when the sensitivity is improved by the resonance adjustment circuit 50, the frequency band is limited to about several kHz. In this respect, in the brain measurement system M1 according to the embodiment, since the plurality of receiving coils 22 having different resonance frequencies are arranged according to the magnetic field gradient, it is possible to ensure a sufficient frequency band, that is, a field of view (FOV) as a whole while improving the sensitivity. As described above, according to the brain measurement system M1 according to the embodiment, it is possible to improve the detection sensitivity and ensure the sufficient FOV.

The plurality of OPM modules 23 may include one OPM module 23 that detects the all signals related to the two or more receiving coils 22 having the same resonance frequency related to the resonance adjustment circuit 50 by adjusting the phase. In this manner, the signals related to the receiving coils 22 having the same resonance frequency are detected by the same OPM module 23 while adjusting the phase, so that the brain measurement can be performed with a simple configuration by reducing the number of OPM modules 23 which are detection units.

The frequency band in which the detection sensitivity of the OPM module 23 is maximized may include the resonance frequency related to the corresponding resonance adjustment circuit 50. Accordingly, it is possible to further improve the detection sensitivity in the detection unit.

The receiving coil 22 may be formed so that the maximum area and the number of turns on the plane perpendicular to the X-axis direction which is the direction in which the static magnetic field is generated are constant. With such a configuration, the sensitivity of the receiving coil 22 becomes uniform, and the brain measurement can be more appropriately performed.

Further, in the resonance adjustment circuit 50 of the brain measurement system M1 according to the embodiment, the capacitances of the capacitors Cs1 and Cp1 of the input side circuit 52 may be adjusted so that the input impedance which is impedance when the input side circuit 52 and the receiving coil 22 side are viewed from the coaxial cable 51 becomes the same as the impedance of the coaxial cable 51 at the resonance frequency, and the capacitances of the capacitors Cs2 and Cp2 of the output side circuit 55 may be adjusted so that the output impedance which is the impedance when the output side circuit 55 and the output coil 24 side are viewed from the coaxial cable 51 becomes the same as the impedance of the coaxial cable 51 at the resonance frequency. In this manner, the capacitances of the impedances Cs1, Cp1, Cs2, and Cp2 of the input side circuit 52 and the output side circuit 55 are adjusted so that both the input impedance viewed from the input side circuit 52 and the receiving coil 22 side from the coaxial cable 51 and the output impedance viewed from the output side circuit 55 and the output coil 24 side are the same as the impedance of the coaxial cable 51 at the resonance frequency. With such a configuration, since both the input impedance and the output impedance viewed from the coaxial cable 51 become the same as the impedance of the coaxial cable 51 at the resonance frequency, the power loss due to the signal reflection for the component of the resonance frequency in the signal can be suppressed, and the detection sensitivity in the OPM module 23 can be improved.

Figure 11A:
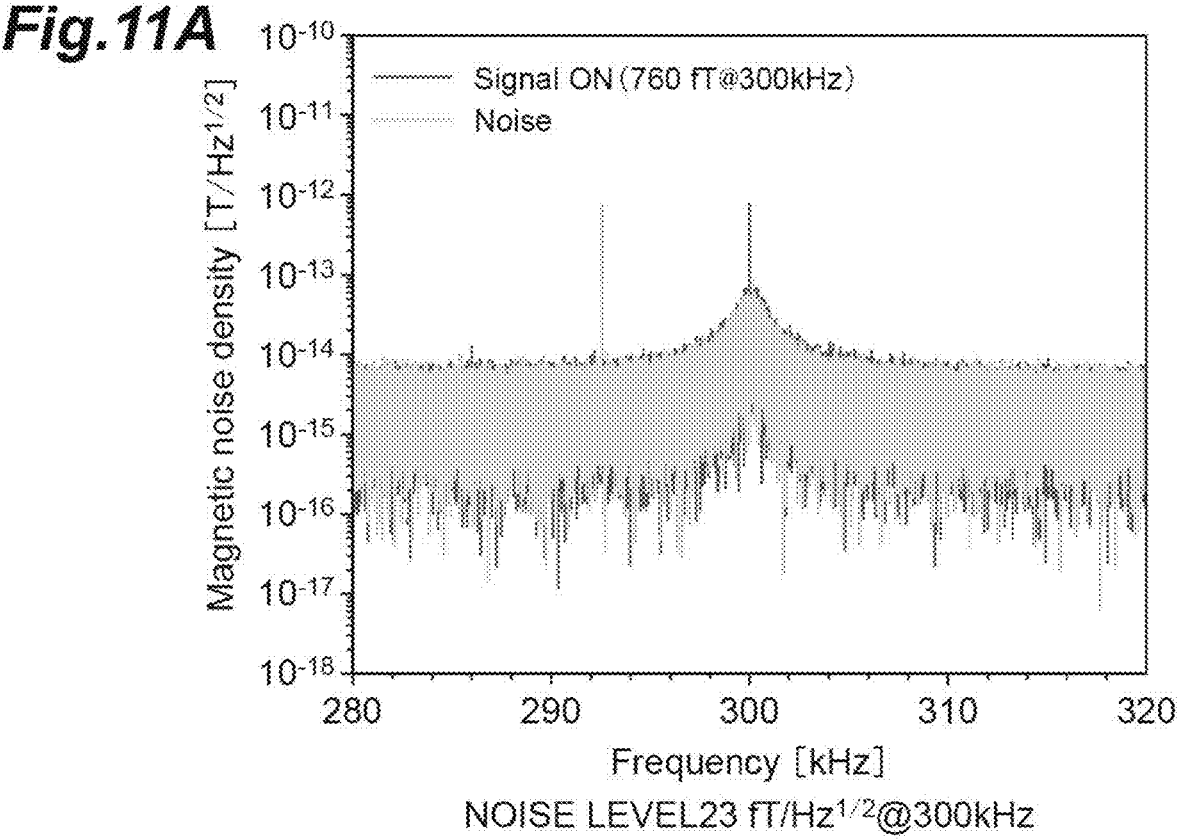
FIGS. 11A and 11B are diagrams illustrating functions and effects of the brain measurement system according to the embodiment.
Figure 11B:
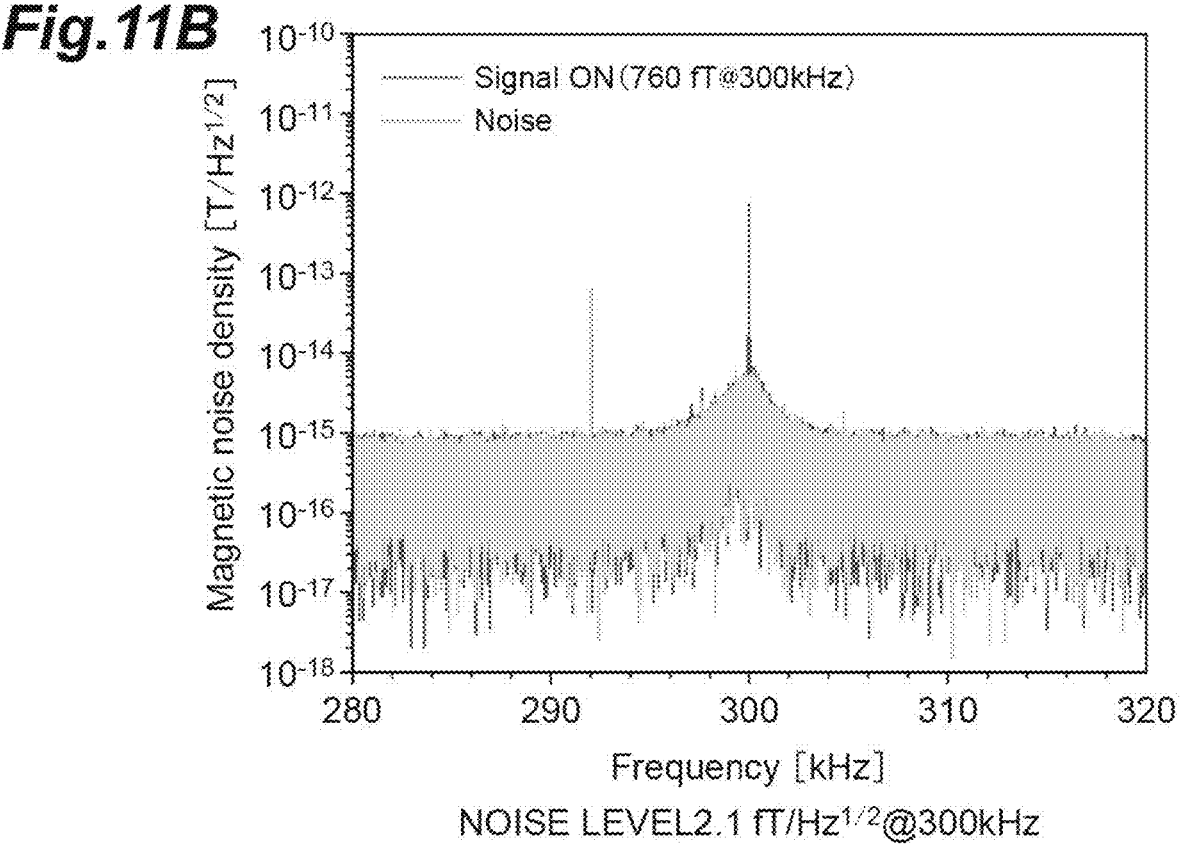

FIGS. 11A and 11B are diagrams illustrating the functions and effects of the brain measurement system M1 according to the embodiment. FIG. 11A illustrates a noise level in a series resonance configuration (configuration according to Comparative Example) in which the capacitor is connected in series between the receiving coil 22 and the output coil 24. FIG. 11B illustrates a noise level in a configuration including the resonance adjustment circuit 50 (resonance adjustment circuit 50 illustrated in FIGS. 9 and 10) according to the embodiment. In FIGS. 11A and 11B, the horizontal axis represents a frequency, and the vertical axis represents a magnetic noise density. As illustrated in FIG. 11A, in the configuration according to Comparative Example, the noise level is 23 fT/Hz$^{1/2}$ under the condition that the frequency is 300 kHz. On the other hand, as illustrated in FIG. 11B, in the configuration according to the embodiment, the noise level is 2.1 fT/Hz$^{1/2}$ under the condition that the frequency is 300 kHz. As described above, in the configuration according to the embodiment, the SNR can be significantly improved as compared with the configuration according to Comparative Example. That is, in the configuration according to the embodiment, since the signal reflection between the FT input/output coils (receiving coil 22 and output coil 24) is suppressed, and the FT gain is increased, the sensitivity in the OPM module 23 can be increased. Further, even if the coaxial cable 51 between the FT input/output coils is lengthened, since the signal loss can be reduced, the degree of freedom in arranging the input/output coils and the OPM module 23 is increased.

Heretofore, although the embodiments of the disclosure have been described, the disclosure is not limited to the above embodiments. For example, although the brain measurement system M1 including the resonance adjustment circuit 50 has been described, the resonance adjustment circuit 50 may be provided in another AC magnetic field measurement device other than the brain measurement system M1.

Figure 12:
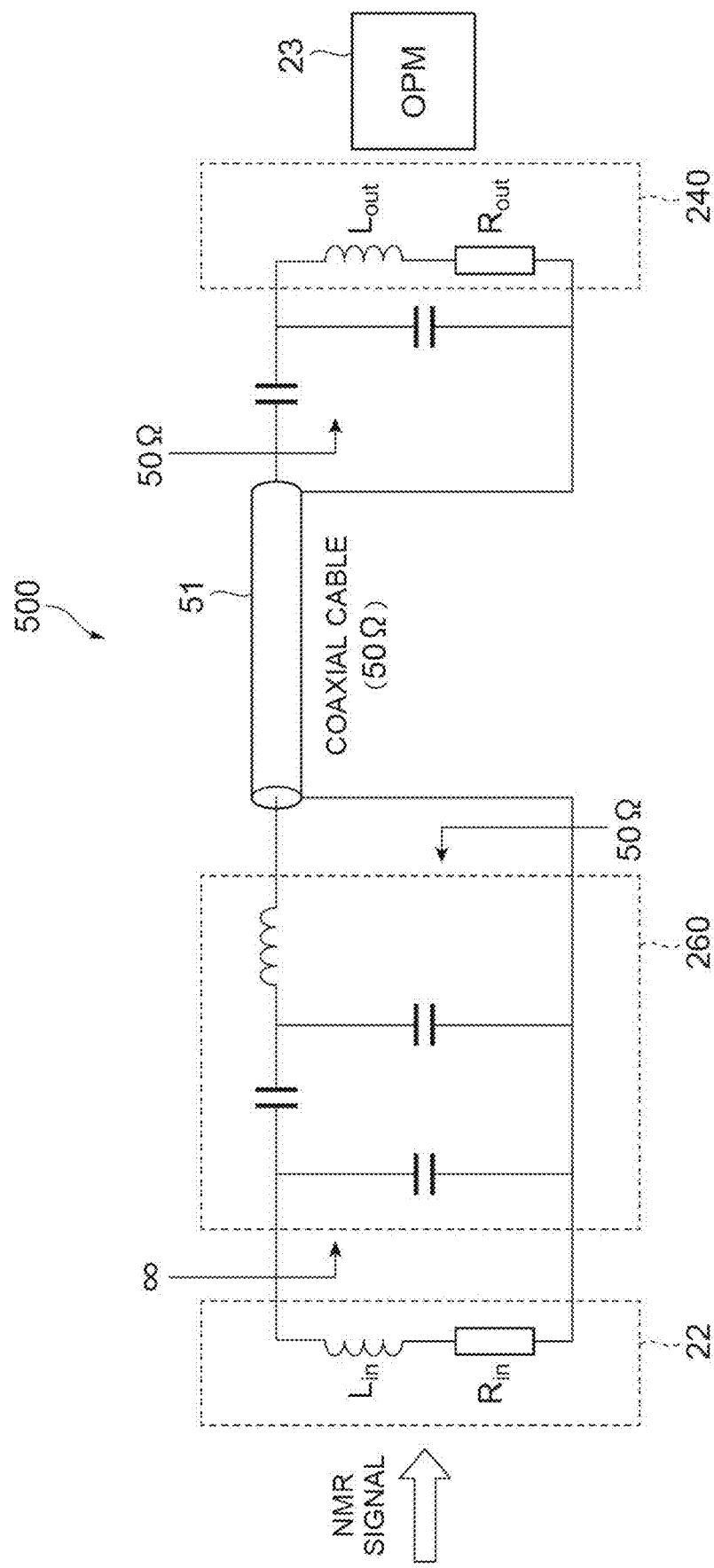
FIG. 12 is a diagram illustrating a detailed circuit configuration of a resonance adjustment circuit according to Modified Example.

Further, the configuration of the resonance adjustment circuit is not limited to the configuration illustrated in FIG. 10. FIG. 12 is a diagram illustrating a detailed circuit configuration of a resonance adjustment circuit 500 according to Modified Example. As illustrated in FIG. 12, the resonance adjustment circuit 500 provided between the receiving coil 22 and the output coil 240 has an impedance matching circuit 260 connected to the receiving coil 22. The impedance matching circuit 260 has high impedance on the rear side (coaxial cable 51 side) when viewed from the receiving coil 22. By providing such an impedance matching circuit 260, the current flowing through the coils can be reduced, and inductive coupling between the coils can be reduced when a coil array is used. In addition, even in such a configuration, by matching the impedance of the coaxial cable 51 and the impedance of the output coil 240, the current can be efficiently passed through the output coil 240.

Figure 13:
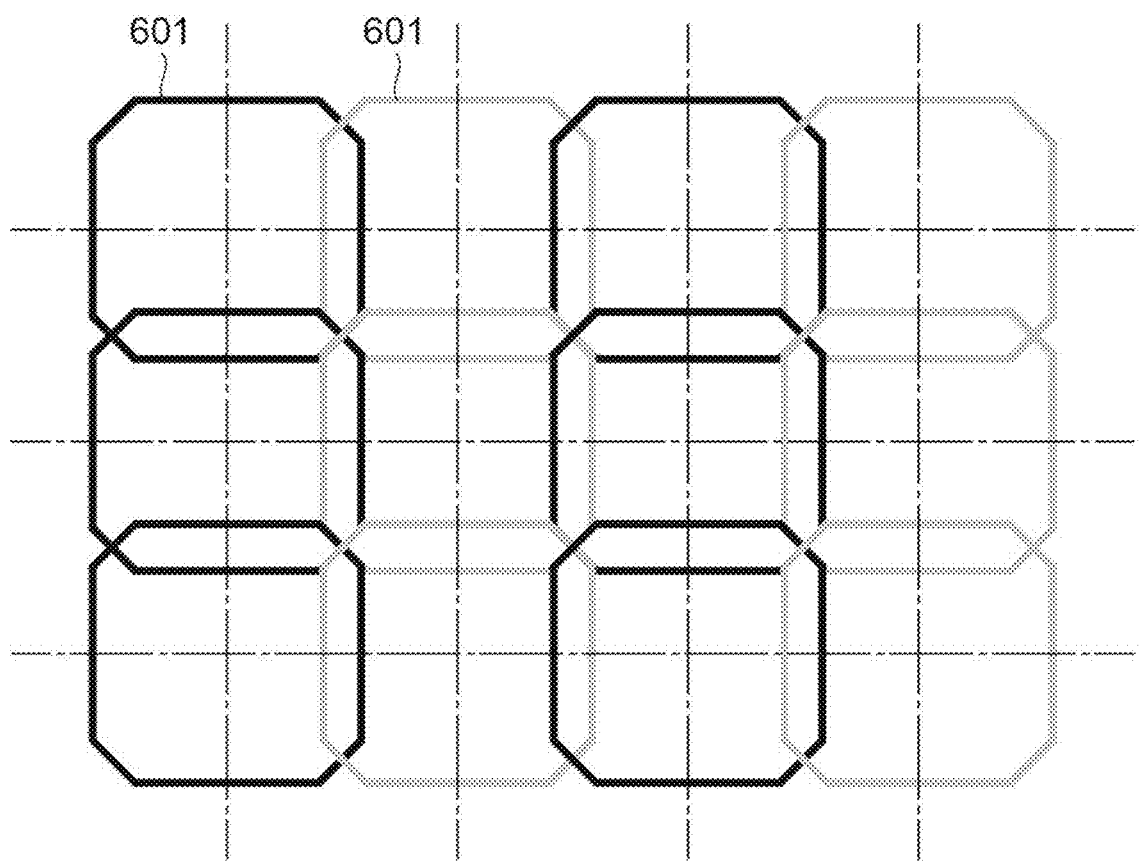
FIG. 13 is a diagram illustrating a configuration of a receiving coil according to Modified Example.

Further, the configuration of the receiving coil may be the configuration of the phased array coil as illustrated in FIG. 13. FIG. 13 is a diagram illustrating a configuration of the receiving coil (phased array coil) according to Modified Example. In the configuration of the phased array coil illustrated in FIG. 13, the coils 601 are arranged to overlap each other in consideration of the interference between the adjacent coils 601 and 601. In this manner, by arranging the coils 601 with the specific overlap, the induced electromotive forces from the adjacent coils 601 can be canceled, and the electrical interference can be minimized.

What is claimed is:

1. A brain measurement system comprising:
   a static magnetic field coil for applying a static magnetic field;
   a gradient magnetic field coil for applying a gradient magnetic field;
   a transmission coil for transmitting a transmission pulse having a predetermined frequency;
   a plurality of receiving coils for detecting a nuclear magnetic resonance signal generated by transmission of the transmission pulse and converting the nuclear magnetic resonance signal into a current;
   a plurality of resonance adjustment circuits provided corresponding to each of the plurality of receiving coils for outputting a signal having a predetermined resonance frequency of a current output from the receiving coil;
   a plurality of detection units provided corresponding to each of the plurality of resonance adjustment circuits for detecting the signal having the resonance frequency output from the resonance adjustment circuit; and
   a control device configured to control currents to be supplied to the static magnetic field coil and the gradient magnetic field coil to control the static magnetic field and a tilted magnetic field and control a current to be supplied to the transmission coil so that the transmission pulse is transmitted to a head portion of a subject to generate an MR image based on the signal detected by the detection unit,
   wherein, when a direction parallel to a central axis of the head portion of the subject is defined as a Z-axis direction, the resonance frequency related to each of the plurality of resonance adjustment circuits is set according to a magnetic field gradient in the Z-axis direction generated by control of a position of the corresponding receiving coil in the Z-axis direction and the tilted magnetic field.

2. The brain measurement system according to claim 1, wherein the plurality of detection units include one detection unit configured to detect all signals related to the two or more receiving coils having the same resonance frequency related to the resonance adjustment circuit by adjusting phases.

3. The brain measurement system according to claim 1, wherein a frequency band in which a detection sensitivity of the detection unit is maximized includes the resonance frequency related to the corresponding resonance adjustment circuit.

4. The brain measurement system according to claim 1, wherein the receiving coil is formed so that a maximum area and the number of turns on a plane perpendicular to a direction in which the static magnetic field is generated are constant.

5. The brain measurement system according to claim 1, wherein the receiving coil is a phased array coil.

* * * * *